US012733882B2

(12) United States Patent
Lee et al.

(10) Patent No.: US 12,733,882 B2
(45) Date of Patent: Sep. 15, 2026

(54) METHODS AND DEVICES TO DETECT POOR CEREBRAL BLOOD FLOW IN REAL-TIME TO PREVENT DIZZINESS, FAINTING, AND FALLS

(71) Applicant: Lumia Health, Inc., Allston, MA (US)

(72) Inventors: Daniel Lee, Brighton, MA (US); Paul Jin, Waban, MA (US); Joshua B. Minuskin, North Easton, MA (US)

(73) Assignee: Lumia Health, Inc., Allston, MA (US)

( * ) Notice: Subject to any disclaimer, the term of this patent is extended or adjusted under 35 U.S.C. 154(b) by 379 days.

(21) Appl. No.: 18/044,476

(22) PCT Filed: Sep. 10, 2021

(86) PCT No.: PCT/US2021/049830

§ 371 (c)(1),
(2) Date: Mar. 8, 2023

(87) PCT Pub. No.: WO2022/056241

PCT Pub. Date: Mar. 17, 2022

(65) Prior Publication Data

US 2023/0355187 A1 Nov. 9, 2023

Related U.S. Application Data

(60) Provisional application No. 63/077,436, filed on Sep. 11, 2020.

(51) Int. Cl.

| | |
|---|---|
| ***A61B 5/00*** | (2006.01) |
| ***A61B 5/0205*** | (2006.01) |
| ***A61B 5/11*** | (2006.01) |

(52) U.S. Cl.

CPC .......... *A61B 5/7282* (2013.01); *A61B 5/0205* (2013.01); *A61B 5/1116* (2013.01);

(Continued)

(58) Field of Classification Search

CPC ... A61B 5/7282; A61B 5/0205; A61B 5/1116; A61B 5/6816; A61B 5/7275; A61B 5/7405; A61B 5/742

See application file for complete search history.

(56) References Cited

U.S. PATENT DOCUMENTS

| | | | |
|---|---|---|---|
| 8,157,730 | B2 | 4/2012 | LeBoeuf et al. |
| 8,204,786 | B2 | 6/2012 | LeBoeuf et al. |

(Continued)

FOREIGN PATENT DOCUMENTS

| | | |
|---|---|---|
| CN | 104168828 A | 11/2014 |
| CN | 104203088 A | 12/2014 |

(Continued)

OTHER PUBLICATIONS

Burt: Apple settles with Valencell in wearable biometric patent infringement suit. Biometric (2019).

(Continued)

*Primary Examiner* — Amanda L Steinberg
*Assistant Examiner* — Laura Hodge
(74) *Attorney, Agent, or Firm* — Scale LLP

(57) ABSTRACT

Provided herein are methods, devices, systems, and platforms for real-time monitoring of cerebral blood flow to prevent dizziness, fainting and falls.

20 Claims, 16 Drawing Sheets

(52) U.S. Cl.
CPC .......... *A61B 5/6816* (2013.01); *A61B 5/7275* (2013.01); *A61B 5/7405* (2013.01); *A61B 5/742* (2013.01)

(56) References Cited

U.S. PATENT DOCUMENTS

| | | | |
|---|---|---|---|
| D666,169 S | 8/2012 | Tucker et al. | |
| 8,251,903 B2 | 8/2012 | LeBoeuf et al. | |
| 8,320,982 B2 | 11/2012 | LeBoeuf et al. | |
| 8,323,982 B2 | 12/2012 | LeBoeuf et al. | |
| 8,512,242 B2 | 8/2013 | LeBoeuf et al. | |
| 8,647,270 B2 | 2/2014 | LeBoeuf et al. | |
| 8,652,040 B2 | 2/2014 | LeBoeuf et al. | |
| 8,652,409 B2 | 2/2014 | LeBoeuf et al. | |
| 8,700,111 B2 | 4/2014 | LeBoeuf et al. | |
| 8,702,607 B2 | 4/2014 | LeBoeuf et al. | |
| 8,788,002 B2 | 7/2014 | LeBoeuf et al. | |
| 8,886,269 B2 | 11/2014 | LeBoeuf et al. | |
| 8,888,701 B2 | 11/2014 | LeBoeuf et al. | |
| D719,860 S | 12/2014 | Just et al. | |
| 8,923,941 B2 | 12/2014 | LeBoeuf et al. | |
| 8,929,965 B2 | 1/2015 | LeBoeuf et al. | |
| 8,929,966 B2 | 1/2015 | LeBoeuf et al. | |
| 8,934,952 B2 | 1/2015 | LeBoeuf et al. | |
| 8,942,776 B2 | 1/2015 | LeBoeuf et al. | |
| 8,961,415 B2 | 2/2015 | LeBoeuf et al. | |
| 8,989,830 B2 | 3/2015 | LeBoeuf et al. | |
| 9,044,180 B2 | 6/2015 | LeBoeuf et al. | |
| D733,598 S | 7/2015 | Just et al. | |
| D736,935 S | 8/2015 | Just et al. | |
| 9,131,312 B2 | 9/2015 | LeBoeuf et al. | |
| 9,289,135 B2 | 3/2016 | LeBoeuf et al. | |
| 9,289,175 B2 | 3/2016 | LeBoeuf et al. | |
| 9,301,696 B2 | 4/2016 | LeBoeuf et al. | |
| 9,314,167 B2 | 4/2016 | LeBoeuf et al. | |
| 9,427,191 B2 | 8/2016 | LeBoeuf | |
| 9,521,962 B2 | 12/2016 | LeBoeuf | |
| 9,538,921 B2 | 1/2017 | LeBoeuf et al. | |
| 9,554,205 B2 | 1/2017 | Urup et al. | |
| 9,750,462 B2 | 9/2017 | LeBoeuf et al. | |
| 9,788,785 B2 | 10/2017 | LeBoeuf | |
| 9,788,794 B2 | 10/2017 | LeBoeuf et al. | |
| 9,794,653 B2 | 10/2017 | Aumer et al. | |
| 9,801,552 B2 | 10/2017 | Romesburg | |
| 9,808,204 B2 | 11/2017 | LeBoeuf et al. | |
| 9,955,919 B2 | 5/2018 | LeBoeuf et al. | |
| 9,993,204 B2 | 6/2018 | Romesburg | |
| 10,003,882 B2 | 6/2018 | Urup et al. | |
| 10,015,582 B2 | 7/2018 | Wagner et al. | |
| 10,076,253 B2 | 9/2018 | Just et al. | |
| 10,076,282 B2 | 9/2018 | LeBoeuf et al. | |
| 10,092,245 B2 | 10/2018 | LeBoeuf et al. | |
| 10,206,627 B2 | 2/2019 | LeBoeuf et al. | |
| 10,219,069 B2 | 2/2019 | Urup et al. | |
| 10,219,709 B2 | 3/2019 | Basu | |
| 10,258,243 B2 | 4/2019 | LeBoeuf et al. | |
| 10,349,844 B2 | 7/2019 | Romesburg | |
| 10,382,839 B2 | 8/2019 | Aumer et al. | |
| 10,390,762 B2 | 8/2019 | Romesburg | |
| 10,413,197 B2 | 9/2019 | LeBoeuf et al. | |
| 10,441,224 B2 | 10/2019 | LeBoeuf et al. | |
| 10,448,840 B2 | 10/2019 | LeBoeuf et al. | |
| 10,512,403 B2 | 12/2019 | Romesburg | |
| 10,536,768 B2 | 1/2020 | Wagner et al. | |
| 10,542,893 B2 | 1/2020 | LeBoeuf et al. | |
| 10,595,730 B2 | 3/2020 | LeBoeuf et al. | |
| 10,610,158 B2 | 4/2020 | Aumer et al. | |
| 10,623,849 B2 | 4/2020 | Wagner et al. | |
| 10,716,480 B2 | 7/2020 | LeBoeuf et al. | |
| 10,716,481 B2 | 7/2020 | LeBoeuf et al. | |
| 11,330,993 B2 | 5/2022 | Basu | |
| 2007/0197881 A1 | 8/2007 | Wolf et al. | |
| 2008/0146890 A1* | 6/2008 | LeBoeuf | A61B 5/0002 600/300 |
| 2008/0146892 A1 | 6/2008 | LeBoeuf et al. | |
| 2008/0220535 A1 | 9/2008 | LeBoeuf et al. | |
| 2009/0112071 A1 | 4/2009 | LeBoeuf et al. | |
| 2009/0227853 A1* | 9/2009 | Wijesiriwardana | A61B 5/02427 600/323 |
| 2010/0049017 A1 | 2/2010 | LeBoeuf et al. | |
| 2010/0217098 A1 | 8/2010 | LeBoeuf et al. | |
| 2010/0217099 A1 | 8/2010 | LeBoeuf et al. | |
| 2010/0217100 A1 | 8/2010 | LeBoeuf et al. | |
| 2010/0217102 A1 | 8/2010 | LeBoeuf et al. | |
| 2011/0106627 A1 | 5/2011 | LeBoeuf et al. | |
| 2012/0197093 A1 | 8/2012 | LeBoeuf et al. | |
| 2012/0197737 A1 | 8/2012 | LeBoeuf et al. | |
| 2012/0283577 A1 | 11/2012 | LeBoeuf et al. | |
| 2012/0283578 A1 | 11/2012 | LeBoeuf et al. | |
| 2012/0296184 A1 | 11/2012 | LeBoeuf et al. | |
| 2013/0059396 A1 | 3/2013 | LeBoeuf et al. | |
| 2013/0131519 A1 | 5/2013 | LeBoeuf et al. | |
| 2014/0012105 A1 | 1/2014 | LeBoeuf et al. | |
| 2014/0051948 A1 | 2/2014 | LeBoeuf et al. | |
| 2014/0058220 A1 | 2/2014 | LeBoeuf et al. | |
| 2014/0094663 A1 | 4/2014 | LeBoeuf et al. | |
| 2014/0114147 A1 | 4/2014 | Romesburg | |
| 2014/0128690 A1 | 5/2014 | LeBoeuf | |
| 2014/0135596 A1 | 5/2014 | LeBoeuf et al. | |
| 2014/0140567 A1 | 5/2014 | LeBoeuf et al. | |
| 2014/0171755 A1 | 6/2014 | LeBoeuf et al. | |
| 2014/0171762 A1 | 6/2014 | LeBoeuf et al. | |
| 2014/0180039 A1 | 6/2014 | LeBoeuf et al. | |
| 2014/0235967 A1 | 8/2014 | LeBoeuf et al. | |
| 2014/0235968 A1 | 8/2014 | LeBoeuf et al. | |
| 2014/0243617 A1 | 8/2014 | LeBoeuf et al. | |
| 2014/0243620 A1 | 8/2014 | LeBoeuf et al. | |
| 2014/0249381 A1 | 9/2014 | LeBoeuf et al. | |
| 2014/0257850 A1 | 9/2014 | Walker et al. | |
| 2014/0275855 A1 | 9/2014 | LeBoeuf et al. | |
| 2014/0287833 A1 | 9/2014 | LeBoeuf et al. | |
| 2014/0288394 A1 | 9/2014 | LeBoeuf et al. | |
| 2014/0288395 A1 | 9/2014 | LeBoeuf et al. | |
| 2014/0288396 A1 | 9/2014 | LeBoeuf et al. | |
| 2014/0323829 A1 | 10/2014 | LeBoeuf et al. | |
| 2014/0323830 A1 | 10/2014 | LeBoeuf et al. | |
| 2015/0011898 A1 | 1/2015 | Romesburg | |
| 2015/0018636 A1 | 1/2015 | Romesburg | |
| 2015/0031967 A1 | 1/2015 | LeBoeuf et al. | |
| 2015/0032009 A1 | 1/2015 | LeBoeuf et al. | |
| 2015/0073236 A1 | 3/2015 | LeBoeuf et al. | |
| 2015/0080741 A1 | 3/2015 | LeBoeuf et al. | |
| 2015/0105633 A1 | 4/2015 | LeBoeuf et al. | |
| 2015/0119657 A1 | 4/2015 | LeBoeuf et al. | |
| 2015/0126824 A1 | 5/2015 | LeBoeuf et al. | |
| 2015/0126825 A1 | 5/2015 | LeBoeuf et al. | |
| 2015/0131837 A1 | 5/2015 | LeBoeuf et al. | |
| 2015/0138556 A1 | 5/2015 | LeBoeuf et al. | |
| 2015/0141772 A1 | 5/2015 | LeBoeuf et al. | |
| 2015/0150469 A1 | 6/2015 | LeBoeuf et al. | |
| 2015/0157222 A1 | 6/2015 | LeBoeuf et al. | |
| 2015/0181325 A1 | 6/2015 | Urup et al. | |
| 2015/0289818 A1 | 10/2015 | LeBoeuf et al. | |
| 2015/0305682 A1 | 10/2015 | LeBoeuf et al. | |
| 2015/0342467 A1 | 12/2015 | LeBoeuf et al. | |
| 2015/0351688 A1 | 12/2015 | Just et al. | |
| 2015/0359489 A1 | 12/2015 | Baudenbacher et al. | |
| 2015/0366471 A1 | 12/2015 | LeBoeuf et al. | |
| 2015/0366475 A1 | 12/2015 | Just et al. | |
| 2015/0366509 A1 | 12/2015 | Romesburg | |
| 2016/0029898 A1 | 2/2016 | LeBoeuf et al. | |
| 2016/0029964 A1 | 2/2016 | LeBoeuf et al. | |
| 2016/0037274 A1 | 2/2016 | Andersson et al. | |
| 2016/0094899 A1 | 3/2016 | Aumer et al. | |
| 2016/0128637 A1 | 5/2016 | LeBoeuf et al. | |
| 2016/0166203 A1 | 6/2016 | Goldstein | |
| 2016/0249128 A1* | 8/2016 | Goldstein | H04R 1/1016 |
| 2016/0256117 A1* | 9/2016 | Baik | A61B 5/6803 |
| 2016/0317049 A1 | 11/2016 | LeBoeuf et al. | |
| 2016/0331274 A1 | 11/2016 | LeBoeuf | |
| 2016/0361020 A1 | 12/2016 | LeBoeuf et al. | |
| 2016/0374621 A1 | 12/2016 | LeBoeuf et al. | |
| 2017/0079582 A1 | 3/2017 | LeBoeuf | |

(56) References Cited

U.S. PATENT DOCUMENTS

2017/0095167 A1 4/2017 Facteau et al.
2017/0112447 A1 4/2017 Aumer et al.
2017/0112671 A1 4/2017 Goldstein
2017/0118551 A1 4/2017 Wagner et al.
2017/0119314 A1 5/2017 Just et al.
2017/0119315 A1 5/2017 LeBoeuf et al.
2017/0188851 A1 7/2017 LeBoeuf et al.
2017/0201840 A1 7/2017 Wenzel et al.
2017/0209095 A1 7/2017 Wagner et al.
2017/0245046 A1 8/2017 Urup et al.
2017/0290549 A1 10/2017 Romesburg
2017/0332974 A1 11/2017 Romesburg
2017/0359635 A1 12/2017 Aumer et al.
2017/0367658 A1 12/2017 LeBoeuf et al.
2018/0008200 A1 1/2018 Romesburg
2018/0020979 A1 1/2018 Wagner et al.
2018/0042554 A1 2/2018 Wagner et al.
2018/0049645 A1 2/2018 Romesburg
2018/0055450 A1 3/2018 LeBoeuf et al.
2018/0078209 A1* 3/2018 Wagner ................ A61B 5/0261
2018/0092601 A1 4/2018 Wagner et al.
2018/0184916 A1 7/2018 LeBoeuf et al.
2018/0192950 A1 7/2018 LeBoeuf et al.
2018/0199837 A1 7/2018 Aumer et al.
2018/0214028 A1 8/2018 Zhang et al.
2018/0220901 A1 8/2018 LeBoeuf et al.
2018/0220902 A1 8/2018 LeBoeuf et al.
2018/0220903 A1 8/2018 LeBoeuf et al.
2018/0220904 A1 8/2018 LeBoeuf et al.
2018/0220905 A1 8/2018 LeBoeuf et al.
2018/0220906 A1 8/2018 LeBoeuf et al.
2018/0228381 A1 8/2018 LeBoeuf et al.
2018/0228435 A1 8/2018 LeBoeuf et al.
2018/0235550 A1 8/2018 Romesburg
2018/0242859 A1 8/2018 LeBoeuf et al.
2018/0242860 A1 8/2018 LeBoeuf et al.
2018/0270566 A1 9/2018 Urup et al.
2018/0296165 A1 10/2018 LeBoeuf et al.
2018/0296166 A1 10/2018 LeBoeuf et al.
2018/0302709 A1 10/2018 Wagner et al.
2018/0303430 A1 10/2018 LeBoeuf et al.
2018/0311502 A1* 11/2018 Brandmeier ....... A61N 1/36132
2018/0325466 A1 11/2018 An et al.
2018/0353134 A1 12/2018 Walter et al.
2018/0360386 A1 12/2018 LeBoeuf et al.
2018/0376235 A1 12/2018 Leabman et al.
2019/0000396 A1 1/2019 LeBoeuf et al.
2019/0053719 A1* 2/2019 Braun ................ A61B 5/02055
2019/0117070 A1 4/2019 Muhsin et al.
2019/0313166 A1* 10/2019 Aumer .................. G08B 21/18
2019/0381314 A1 12/2019 Howard
2020/0092626 A1 3/2020 Bell-Booth
2020/0139126 A1 5/2020 Napadow et al.
2020/0237307 A1* 7/2020 Sato ....................... A61B 5/291
2020/0268315 A1 8/2020 Burwinkel et al.
2021/0219923 A1* 7/2021 Eun Young Yang ........................ A61B 5/7275

FOREIGN PATENT DOCUMENTS

CN 104969035 A 10/2015
CN 105050494 A 11/2015
CN 105324080 A 2/2016
CN 105379306 A 3/2016
CN 104203088 B 9/2017
CN 107260142 A 10/2017
CN 105050494 B 6/2018
CN 108348154 A 7/2018
CN 108937908 A 12/2018
CN 105324080 B 2/2019
CN 104969035 B 5/2019
CN 105379306 B 2/2020
EP 2094152 A1 9/2009
EP 2400884 A2 1/2012
EP 2405805 A2 1/2012
EP 2667768 A2 12/2013
EP 2739207 A2 6/2014
EP 2804526 A1 11/2014
EP 2862504 A2 4/2015
EP 2862504 A3 6/2015
EP 2887692 A1 6/2015
EP 2928364 A1 10/2015
EP 2931125 A2 10/2015
EP 2932729 A1 10/2015
EP 2943753 A2 11/2015
EP 2094152 B1 4/2016
EP 2862504 B1 6/2016
EP 2932729 B1 9/2016
EP 3081155 A1 10/2016
EP 3110313 A1 1/2017
EP 3127476 A1 2/2017
EP 3128761 A1 2/2017
EP 3139822 A1 3/2017
EP 3139823 A1 3/2017
EP 3146896 A1 3/2017
EP 3151737 A1 4/2017
EP 3153093 A1 4/2017
EP 3157412 A1 4/2017
EP 3171767 A1 5/2017
EP 2739207 B1 7/2017
EP 2667768 B1 8/2017
EP 3199100 A1 8/2017
EP 3222210 A1 9/2017
EP 3248539 A1 11/2017
EP 3264974 A1 1/2018
EP 2400884 B1 3/2018
EP 3310252 A1 4/2018
EP 3344127 A1 7/2018
EP 3357419 A1 8/2018
EP 3376947 A1 9/2018
EP 3153093 B1 4/2019
EP 2887692 B1 7/2019
EP 3128761 B1 2/2020
EP 2943753 B1 4/2020
EP 3146896 B1 4/2020
HK 1203800 A1 11/2015
HK 1204252 A1 11/2015
HK 1207811 A1 2/2016
HK 1210351 A1 4/2016
HK 1212878 A1 6/2016
HK 1216705 A1 12/2016
HK 1217038 A1 12/2016
HK 1232106 A1 1/2018
HK 1232107 A1 1/2018
JP 2009153824 A 7/2009
JP 2012518515 A 8/2012
JP 2015506746 A 3/2015
JP 5789199 B2 10/2015
JP 2015231550 A 12/2015
JP 2016013444 A 1/2016
JP 6126651 B2 5/2017
JP 6153573 B2 6/2017
JP 2017159052 A 9/2017
JP 6309668 B2 4/2018
JP 2018108467 A 7/2018
WO WO-2008085411 A2 7/2008
WO WO-2008088511 A1 7/2008
WO WO-2008085411 A3 9/2008
WO WO-2010098912 A2 9/2010
WO WO-2010098915 A1 9/2010
WO WO-2010099066 A2 9/2010
WO WO-2010099190 A2 9/2010
WO WO-2010098912 A3 11/2010
WO WO-2010099066 A3 11/2010
WO WO-2010099190 A3 1/2011
WO WO-2012103273 A2 8/2012
WO WO-2012103273 A3 10/2012
WO WO-2013016007 A2 1/2013
WO WO-2013019494 A2 2/2013
WO WO-2013016007 A3 3/2013
WO WO-2013109389 A1 7/2013
WO WO-2013109390 A1 7/2013
WO WO-2013019494 A3 5/2014

(56) References Cited

FOREIGN PATENT DOCUMENTS

| | | | |
|---|---|---|---|
| WO | WO-2014092932 | A1 | 6/2014 |
| WO | WO-2014109982 | A2 | 7/2014 |
| WO | WO-2014116942 | A2 | 7/2014 |
| WO | WO-2014109982 | A3 | 10/2014 |
| WO | WO-2014116942 | A3 | 12/2014 |
| WO | WO-2015131065 | A1 | 9/2015 |
| WO | WO-2016018756 | A1 | 2/2016 |
| WO | WO-2016018762 | A1 | 2/2016 |
| WO | WO-2016019002 | A1 | 2/2016 |
| WO | WO-2016022295 | A1 | 2/2016 |
| WO | WO-2016048500 | A1 | 3/2016 |
| WO | WO-2016110804 | A1 | 7/2016 |
| WO | WO-2016140835 | A1 | 9/2016 |
| WO | WO-2016140836 | A1 | 9/2016 |
| WO | WO-2016140837 | A1 | 9/2016 |
| WO | WO-2017011431 | A2 | 1/2017 |
| WO | WO-2017027551 | A1 | 2/2017 |
| WO | WO-2017070463 | A1 | 4/2017 |
| WO | WO-2017100519 | A1 | 6/2017 |
| WO | WO-2017180342 | A1 | 10/2017 |
| WO | WO-2018009736 | A1 | 1/2018 |
| WO | WO-2018175196 | A1 | 9/2018 |
| WO | WO-2019217368 | A1 | 11/2019 |

OTHER PUBLICATIONS

Glendenning: Unlocking the potential of wearable technology on caregiving for seniors. Renew Senior Communities (2020).

Holley: CarePredict Set to Buy IP of San Antonio's WiseWear from Bankruptcy. Xconomy (2018).

Hu: Apple, Fitbit Get Heart Sensor Patent Slashed at PTAB. Sterne Kessler, (2018).

Movva: Artificial Intelligence-Powered Wearable Solution for Senior Care. (2019).

Owen: Apple settles Apple Watch heart rate sensor lawsuit with biometrics firm Valencell. (2019).

PCT/US2021/049830 International Search Report and Written Opinion dated Feb. 2, 2022.

PCT/US2021/049841 International Search Report and Written Opinion dated Dec. 14, 2021.

Examination report from corresponding EP Application No. 21867663.3 dated Aug. 8, 2024.

Official communication in corresponding EP Application No. 21867663.3 dated Dec. 9, 2025.

* cited by examiner

METHODS AND DEVICES TO DETECT POOR CEREBRAL BLOOD FLOW IN REAL-TIME TO PREVENT DIZZINESS, FAINTING, AND FALLS

CROSS-REFERENCE TO RELATED APPLICATION

This application claims the benefit of U.S. Provisional Patent Application No. 63/077,436, filed on Sep. 11, 2020, and is a national phase entry of PCT/US2021/049830, filed on Sep. 10, 2021, each of which is hereby incorporated by reference in its entirety.

BACKGROUND

Poor Cerebral Blood Flow (CBF) is a major public health concern, especially for the elderly. Poor Cerebral Blood Flow most often occurs when a transition to standing causes a reduction of blood flow to the head. Some known diseases, conditions, and syndromes that cause Poor Cerebral Blood Flow upon standing include Orthostatic Hypotension (OH), Postural Orthostatic Tachycardia Syndrome (POTS), Orthostatic Cerebral Hypoperfusion Syndrome (OCHOs), Primary Cerebral Autoregulatory Failure (pCAF), Vasovagal Syncope, Carotid Sinus Sensitivity, hypovolemia, drug-induced hypotension, arrhythmias, vascular stenosis, aortic stenosis, Ehlers-Danlos Syndrome, Multiple Sclerosis, Multiple System Atrophy, Parkinson's, dementia, as well as various other neurological disorders that compromise the autonomic system (dysautonomias). Such loss of blood flow often leads to falling, a leading cause of death in the elderly. Approximately 1 in 4 adults over 65 years old fall once in a year causing 4 deaths/hour. Further, 800,000 people are hospitalized each year, and 3 million people are treated in emergency rooms each year, for head injury or hip fracture, requiring an estimated 50 billion dollars in reactive medical costs.

The treatments currently available to patients suffering from Poor Cerebral Blood Flow are limited. Pharmacological approaches are generally not applicable as many patients suffering from Poor Cerebral Blood Flow are also hypertensive and often already taking medications to lower their blood pressure. Thus, medications to increase blood pressure to reduce Poor Cerebral Blood Flow symptoms are contradictory. Mechanical interventions such as compression socks or airbag belts can be helpful but they have limited adoption due to the daily inconvenience of having to don and doff such interventions. Lifestyle modifications such as increased exercise, dietary changes, increased fluid intake, and slowed transitions to standing are helpful, but behavior change is burdensome for patients to adhere to, is hard to quantify the effective benefit relative to the costly effort, and often forgotten in practice. There is a strong need for an effective approach to managing Cerebral Blood Flow that patients will adopt and adhere to.

SUMMARY

One aspect disclosed herein is a method of preventing presyncope, syncope and falls in a subject comprising: receiving biometric data for the subject; aggregating and processing the biometric data; analyzing the data to detect or predict one or more of: poor cerebral blood flow, poor blood pressure, presyncope, syncope, and a fall event. In some embodiments, the method comprises identifying, detecting, or predicting a poor cerebral blood flow event (which may include falls, dizziness, or fainting) that exceeds a cerebral blood flow risk threshold and delivering one or more real-time messages to the subject pertaining to the identified detected or predicted event.

In some embodiments, the biometric data comprises one or more of: cerebral blood flow, blood pressure, blood volume, heart rate, heart rate variability, and blood oxygenation. In some embodiments, the biometric data is generated by a wearable device associated with the subject. In some embodiments, activity data is collected and comprises one or more of: motion, posture, change in posture, activity level, and type of activity. In some embodiments, the activity data is generated by a wearable device associated with the subject. In some embodiments, analyzing the data comprises applying one or more artificial neural networks (ANNs). In some embodiments, analyzing the data comprises identifying trends pertaining to one or more of: the biometric data of the subject, the activity data of the subject, detected or predicted poor cerebral blood flow for the subject, detected or predicted presyncope events for the subject, detected or predicted syncope events for the subject, and detected or predicted fall events for the subject. In some embodiments, the poor cerebral blood flow or fall risk is based, at least in part, on one or more of: a user profile of the subject, the biometric data of the subject, the activity data of the subject, one or more medical records of the subject, and a medical history of the subject. In some embodiments, the one or more real-time messages comprise an audio message delivered utilizing an acoustic transducer configured to deliver audio messages into the ear of the subject. In some embodiments, the device is configured to operate as an open ear audio device, and wherein the audio messages are delivered to the subject with low sound leakage perceived by others near the subject. In some embodiments, the method further comprises determining one or more applicable audio messages for the subject. In some embodiments, the one or more applicable audio messages for the subject comprise biometric feedback, a behavioral coaching recommendation, a warning, or an alert. In some embodiments, the one or more real-time messages comprise a visual message delivered utilizing a display of a device of the subject or a caretaker of the subject. In some embodiments, the method further comprises determining one or more applicable visual messages for the subject. In some embodiments, the one or more applicable visual messages for the subject comprise biometric feedback, a behavioral coaching recommendation, an alert, or a warning. In some embodiments, the method further comprises providing a subject health portal application allowing access to real-time and historical biometric data and activity data and trends for the subject. In some embodiments, the method further comprises providing a healthcare provider portal application allowing access to real-time and historical biometric data and activity data and trends for one or more subjects.

Another aspect provided herein is a wearable device for preventing presyncope, syncope and falls comprising: a biometric sensor configured to monitor at least one biometric parameter of the subject; a movement sensor configured to monitor at least one activity parameter of the subject; a logic element performing state management comprising: maintaining the device in a sleep state; shifting the device to a first wake state intermittently, at a predefined interval, to perform synchronous monitoring of the subject; and shifting the device to a second wake state, when the at least one activity parameter indicates a change in posture of the subject, to perform asynchronous monitoring of the subject; an acoustic transducer configured to deliver audio messages into the ear of the subject; a wireless communications transceiver; and a microcontroller configured to aggregate and process sensor data, and pass processed data to the wireless communications transceiver. In some embodiments, the wearable device further comprises a micro energy storage bank. In some embodiments, the micro energy storage bank comprises a supercapacitor or a micro battery. In some embodiments, the micro energy storage bank has a maximum capacity of no more than 10 milli-Watt-hour (mWh). In some embodiments, the wearable device further comprises an energy harvesting element configured to charge the micro energy storage bank. In some embodiments, the energy harvesting element compromises a photovoltaic cell configured to harvest energy from natural daylight, interior lighting, and infrared emitters. In some embodiments, the energy harvesting element comprises a RF antenna configured to harvest energy from the environment of the device. In some embodiments, the energy harvesting element comprises a thermoelectric generator configured to harvest energy from body heat of the subject. In some embodiments, the energy harvesting element comprises a piezoelectric material configured to harvest energy from motion of the subject. In some embodiments, in the sleep state, the micro energy storage bank is charged. In some embodiments, in the first wake state and the second wake state, the micro energy storage bank powers operation of the biometric sensor, the movement sensor, the acoustic transducer, and the wireless communications transceiver. In some embodiments, the microcontroller is further configured to analyze the data to detect or predict one or more of: poor cerebral blood flow, poor blood pressure, presyncope, syncope, and a fall event. In some embodiments, the change in posture is sitting up from a laying posture, standing from a sitting posture, standing from a kneeling posture, standing from a squatting posture, or standing upright from a bent standing posture. In some embodiments, the audio messages comprise one or more of: biometric feedback, a behavioral coaching recommendation, a warning, and an alert pertaining to one or more of: poor cerebral blood flow, poor blood pressure, presyncope, syncope, and a fall event. In some embodiments, the device is configured to operate as an open ear audio device, and wherein the audio messages are delivered to the subject with low sound leakage perceived by others near the subject. In some embodiments, the wearable device comprises one or more biometric sensors, with the wearable device or the one or more biometric sensors located inside the cymba concha of the subject. In some embodiments, the disposition of the wearable device or the one or more biometric sensors within the cymba concha allows for superior signal quality with minimal noise artifacts in part due to strong vascularization coming off branches of the posterior auricular artery, as well as minimal musculature that could introduce noise artifacts. In some embodiments, disposition of the wearable device or the one or more biometric sensors within the cymba concha allows for the wearable device to co-exist with other in-ear devices such as hearing aids, wired in-ear headphones, or wireless in-ear headphones.

In some embodiments, the predefined interval is between about 1 minute to about 30 minutes. In some embodiments, the predefined interval is between about 1 minute to about 2 minutes, about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 2 minutes to about 5 minutes, about 2 minutes to about 10 minutes, about 2 minutes to about 15 minutes, about 2 minutes to about 20 minutes, about 2 minutes to about 25 minutes, about 2 minutes to about 30 minutes, about 5 minutes to about 10 minutes, about 5 minutes to about 15 minutes, about 5 minutes to about 20 minutes, about 5 minutes to about 25 minutes, about 5 minutes to about 30 minutes, about 10 minutes to about 15 minutes, about 10 minutes to about 20 minutes, about 10 minutes to about 25 minutes, about 10 minutes to about 30 minutes, about 15 minutes to about 20 minutes, about 15 minutes to about 25 minutes, about 15 minutes to about 30 minutes, about 20 minutes to about 25 minutes, about 20 minutes to about 30 minutes, or about 25 minutes to about 30 minutes, including increments therein. In some embodiments, the predefined interval is between about 1 minute, about 2 minutes, about 5 minutes, about 10 minutes, about 15 minutes, about 20 minutes, about 25 minutes, or about 30 minutes. In some embodiments, the predefined interval is between at least about 1 minute, about 2 minutes, about 5 minutes, about 10 minutes, about 15 minutes, about 20 minutes, or about 25 minutes. In some embodiments, the predefined interval is between at most about 2 minutes, about 5 minutes, about 10 minutes, about 15 minutes, about 20 minutes, about 25 minutes, or about 30 minutes.

In some embodiments, the state management further comprises returning the device to the sleep state after performing the synchronous or asynchronous monitoring of the subject for a monitoring period.

In some embodiments, the monitoring period is between about 5 seconds to about 120 seconds. In some embodiments, the monitoring period is between about 5 seconds to about 10 seconds, about 5 seconds to about 20 seconds, about 5 seconds to about 30 seconds, about 5 seconds to about 40 seconds, about 5 seconds to about 50 seconds, about 5 seconds to about 60 seconds, about 5 seconds to about 70 seconds, about 5 seconds to about 80 seconds, about 5 seconds to about 100 seconds, about 5 seconds to about 110 seconds, about 5 seconds to about 120 seconds, about 10 seconds to about 20 seconds, about 10 seconds to about 30 seconds, about 10 seconds to about 40 seconds, about 10 seconds to about 50 seconds, about 10 seconds to about 60 seconds, about 10 seconds to about 70 seconds, about 10 seconds to about 80 seconds, about 10 seconds to about 100 seconds, about 10 seconds to about 110 seconds, about 10 seconds to about 120 seconds, about 20 seconds to about 30 seconds, about 20 seconds to about 40 seconds, about 20 seconds to about 50 seconds, about 20 seconds to about 60 seconds, about 20 seconds to about 70 seconds, about 20 seconds to about 80 seconds, about 20 seconds to about 100 seconds, about 20 seconds to about 110 seconds, about 20 seconds to about 120 seconds, about 30 seconds to about 40 seconds, about 30 seconds to about 50 seconds, about 30 seconds to about 60 seconds, about 30 seconds to about 70 seconds, about 30 seconds to about 80 seconds, about 30 seconds to about 100 seconds, about 30 seconds to about 110 seconds, about 30 seconds to about 120 seconds, about 40 seconds to about 50 seconds, about 40 seconds to about 60 seconds, about 40 seconds to about 70 seconds, about 40 seconds to about 80 seconds, about 40 seconds to about 100 seconds, about 40 seconds to about 110 seconds, about 40 seconds to about 120 seconds, about 50 seconds to about 60 seconds, about 50 seconds to about 70 seconds, about 50 seconds to about 80 seconds, about 50 seconds to about 100 seconds, about 50 seconds to about 110 seconds, about 50 seconds to about 120 seconds, about 60 seconds to about 70 seconds, about 60 seconds to about 80 seconds, about 60 seconds to about 100 seconds, about 60 seconds to about 110 seconds, about 60 seconds to about 120 seconds, about 70 seconds to about 80 seconds, about 70 seconds to about 100 seconds, about 70 seconds to about 110 seconds, about 70 seconds to about 120 seconds, about 80 seconds to about 100 seconds, about 80 seconds to about 110 seconds, about 80 seconds to about 120 seconds, about 100 seconds to about 110 seconds, about 100 seconds to about 120 seconds, or about 110 seconds to about 120 seconds, including increments therein. In some embodiments, the monitoring period is between about 5 seconds, about 10 seconds, about 20 seconds, about 30 seconds, about 40 seconds, about 50 seconds, about 60 seconds, about 70 seconds, about 80 seconds, about 100 seconds, about 110 seconds, or about 120 seconds. In some embodiments, the monitoring period is between at least about 5 seconds, about 10 seconds, about 20 seconds, about 30 seconds, about 40 seconds, about 50 seconds, about 60 seconds, about 70 seconds, about 80 seconds, about 100 seconds, or about 110 seconds. In some embodiments, the monitoring period is between at most about 10 seconds, about 20 seconds, about 30 seconds, about 40 seconds, about 50 seconds, about 60 seconds, about 70 seconds, about 80 seconds, about 100 seconds, about 110 seconds, or about 120 seconds.

In some embodiments, the wearable device further comprises an attachment mechanism for attaching the device to the subject. In some embodiments, the device is adapted to attach or anchor to an auricle of the subject. In some embodiments, the device is adapted to attach to the auricle of the subject at the cymba concha, scapha, triangular fossa, anti-helix, or inner surface of a helix of the subject.

In some embodiments, the device has a longest dimension of about 6 mm to about 30 mm. In some embodiments, the device has a longest dimension of about 6 mm to about 8 mm, about 6 mm to about 10 mm, about 6 mm to about 12 mm, about 6 mm to about 15 mm, about 6 mm to about 20 mm, about 6 mm to about 25 mm, about 6 mm to about 30 mm, about 8 mm to about 10 mm, about 8 mm to about 12 mm, about 8 mm to about 15 mm, about 8 mm to about 20 mm, about 8 mm to about 25 mm, about 8 mm to about 30 mm, about 10 mm to about 12 mm, about 10 mm to about 15 mm, about 10 mm to about 20 mm, about 10 mm to about 25 mm, about 10 mm to about 30 mm, about 12 mm to about 15 mm, about 12 mm to about 20 mm, about 12 mm to about 25 mm, about 12 mm to about 30 mm, about 15 mm to about 20 mm, about 15 mm to about 25 mm, about 15 mm to about 30 mm, about 20 mm to about 25 mm, about 20 mm to about 30 mm, or about 25 mm to about 30 mm, including increments therein. In some embodiments, the device has a longest dimension of about 6 mm, about 8 mm, about 10 mm, about 12 mm, about 15 mm, about 20 mm, about 25 mm, or about 30 mm. In some embodiments, the device has a longest dimension of at least about 6 mm, about 8 mm, about 10 mm, about 12 mm, about 15 mm, about 20 mm, or about 25 mm. In some embodiments, the device has a longest dimension of at most about 8 mm, about 10 mm, about 12 mm, about 15 mm, about 20 mm, about 25 mm, or about 30 mm.

In some embodiments, the biometric sensor comprises an optical sensor. In some embodiments, the optical sensor comprises a photoplethysmography (PPG) sensor. In some embodiments, the at least one biometric parameter of the subject comprises one or more of: cerebral blood flow, blood pressure, blood volume, heart rate, heart rate variability, and blood oxygenation.

In some embodiments, in the first wake state or the second wake state, the biometric sensor monitors the at least one biometric parameter of the subject at a rate of between about 1 Hz to about 200 Hz. In some embodiments, in the first wake state or the second wake state, the biometric sensor monitors the at least one biometric parameter of the subject at a rate of between about 1 Hz to about 10 Hz, about 1 Hz to about 50 Hz, about 1 Hz to about 100 Hz, about 1 Hz to about 150 Hz, about 1 Hz to about 200 Hz, about 10 Hz to about 50 Hz, about 10 Hz to about 100 Hz, about 10 Hz to about 150 Hz, about 10 Hz to about 200 Hz, about 50 Hz to about 100 Hz, about 50 Hz to about 150 Hz, about 50 Hz to about 200 Hz, about 100 Hz to about 150 Hz, about 100 Hz to about 200 Hz, or about 150 Hz to about 200 Hz, including increments therein. In some embodiments, in the first wake state or the second wake state, the biometric sensor monitors the at least one biometric parameter of the subject at a rate of between about 1 Hz, about 10 Hz, about 50 Hz, about 100 Hz, about 150 Hz, or about 200 Hz. In some embodiments, in the first wake state or the second wake state, the biometric sensor monitors the at least one biometric parameter of the subject at a rate of between at least about 1 Hz, about 10 Hz, about 50 Hz, about 100 Hz, or about 150 Hz. In some embodiments, in the first wake state or the second wake state, the biometric sensor monitors the at least one biometric parameter of the subject at a rate of between at most about 10 Hz, about 50 Hz, about 100 Hz, about 150 Hz, or about 200 Hz.

In some embodiments, the movement sensor comprises at least one accelerometer. In some embodiments, the movement sensor comprises at least one altimeter. In some embodiments, the at least one activity parameter of the subject comprises an activity level.

In some embodiments, in the first wake state or the second wake state, the movement sensor monitors the at least one activity parameter of the subject at a rate of between about 1 Hz to about 200 Hz. In some embodiments, in the first wake state or the second wake state, the movement sensor monitors the at least one activity parameter of the subject at a rate of between about 1 Hz to about 10 Hz, about 1 Hz to about 50 Hz, about 1 Hz to about 100 Hz, about 1 Hz to about 150 Hz, about 1 Hz to about 200 Hz, about 10 Hz to about 50 Hz, about 10 Hz to about 100 Hz, about 10 Hz to about 150 Hz, about 10 Hz to about 200 Hz, about 50 Hz to about 100 Hz, about 50 Hz to about 150 Hz, about 50 Hz to about 200 Hz, about 100 Hz to about 150 Hz, about 100 Hz to about 200 Hz, or about 150 Hz to about 200 Hz, including increments therein. In some embodiments, in the first wake state or the second wake state, the movement sensor monitors the at least one activity parameter of the subject at a rate of between about 1 Hz, about 10 Hz, about 50 Hz, about 100 Hz, about 150 Hz, or about 200 Hz. In some embodiments, in the first wake state or the second wake state, the movement sensor monitors the at least one activity parameter of the subject at a rate of between at least about 1 Hz, about 10 Hz, about 50 Hz, about 100 Hz, or about 150 Hz. In some embodiments, in the first wake state or the second wake state, the movement sensor monitors the at least one activity parameter of the subject at a rate of between at most about 10 Hz, about 50 Hz, about 100 Hz, about 150 Hz, or about 200 Hz.

In some embodiments, the wireless communications transceiver utilizes a Near-Field Communication (NFC) protocol, Bluetooth, Bluetooth Low Energy, LoRa, or Wi-Fi. In some embodiments, the wireless communications transceiver is configured to send data to an external device and receive data from the external device. In some embodiments, the external device comprises a local base station, a mobile device of the subject, or at least one server. In some embodiments, the wearable device further comprises a temperature sensor. In some embodiments, the at least one biometric parameter of the subject comprises temperature.

Another aspect provided herein is a system for preventing presyncope, syncope and falls in a subject comprising a wearable device and a local base station: the wearable device comprising: a biometric sensor configured to monitor at least one biometric parameter of the subject; a movement sensor configured to monitor at least one activity parameter of the subject; a logic element performing state management comprising: maintaining the device in a sleep state; shifting the device to a first wake state intermittently, at a predefined interval, to perform synchronous monitoring of the subject; and shifting the device to a second wake state, when the at least one activity parameter indicates a change in posture of the subject, to perform asynchronous monitoring of the subject; an acoustic transducer configured to deliver audio messages into the ear of the subject; a wireless communications transceiver; and a microcontroller configured to aggregate and process sensor data, and pass processed data to the wireless communications transceiver; and the local base station comprising: a wireless communications transceiver configured to send data to the wearable device and receive data from wearable device; and a network interface configured to provide connectivity to a computer network.

In some embodiments, the local base station further comprises a wireless power transmitter (WPT) comprising an RF energy transmission antenna. In some embodiments, the local base station further comprises a wireless power transmitter (WPT) comprising infrared light emitters. In some embodiments, the infrared light emitters comprise infrared light-emitting diodes (LEDs). In some embodiments, the local base station further comprises an acoustic transducer for broadcasting audio messages. In some embodiments, the local base station further comprises a screen for displaying biometric information and notifications. In some embodiments, the wearable device further comprises an adhesive for attaching the device to an auricle of the subject. In some embodiments, the local base station further comprises one or more processors configured to transmit an alert via one or more of: SMS, MIMS, email, telephone, voice mail, and social media. In some embodiments, the computer network comprises the internet.

Another aspect provided herein is a platform for predicting syncope and fall events in a subject comprising a wearable device, a local base station, and a cloud computing back-end: the wearable device comprising: a biometric sensor configured to monitor at least one biometric parameter of the subject; a movement sensor configured to monitor at least one activity parameter of the subject; a logic element performing state management comprising: maintaining the device in a sleep state; shifting the device to a first wake state intermittently, at a predefined interval, to perform synchronous monitoring of the subject; and shifting the device to a second wake state, when the at least one activity parameter indicates a change in posture of the subject, to perform asynchronous monitoring of the subject; and an acoustic transducer configured to deliver audio messages into the ear of the subject; a wireless communications transceiver; and a microcontroller configured to aggregate and process sensor data, and pass processed data to the wireless communications transceiver; the local base station comprising: a wireless communications transceiver configured to receive the biometric and activity data of the subject from the wearable device and send data to the wearable device; and a network interface configured to provide connectivity to the cloud computing back-end; and a cloud computing back-end comprising: a module configured to store and analyze the biometric and activity data of the subject to identify trends and provide resulting biometric feedback or behavioral coaching recommendations; and a module configured to determine one or more applicable audio messages for the subject.

In some embodiments, the biometric sensor comprises an optical sensor. In some embodiments, the optical sensor comprises a photoplethysmography (PPG) sensor. In some embodiments, the wearable device further comprises an attachment mechanism for attaching the device to an auricle of the subject. In some embodiments, the local base station further comprises one or more processors configured to transmit an alert via one or more of: SMS, MMS, email, telephone, voice mail, and social media. In some embodiments, the computer network comprises the internet. In some embodiments, the analysis comprises identifying trends pertaining to one or more of: the biometric data of the subject, the activity data of the subject, the cerebral blood flow patterns of the subject, the predicted or actual presyncope events for the subject, the predicted or actual syncope events for the subject, or the predicted or actual fall events for the subject. In some embodiments, the cloud computing back-end further comprises a module configured to provide a healthcare provider portal application allowing access to real-time and historical data and trends for one or more subjects. In some embodiments, the cloud computing back-end further comprises a module configured to provide a subject health portal application allowing access to real-time and historical data and trends for the subject. In some embodiments, the biometric feedback or behavioral coaching recommendations pertain to prevention of poor cerebral blood flow, a presyncope event, or a syncope event from resulting in a fall. In some embodiments, the biometric feedback or behavioral coaching recommendations are delivered to the subject via the acoustic transducer in the form of one or more audio messages. In some embodiments, the biometric feedback or behavioral coaching recommendation may be conducted by reading to the subject one or more of their biometric parameters measured in that moment. In some embodiments, relative CBF percentage changes are read to the subject in real-time so the subject can determine if/when they should take action to avoid fainting. In some embodiments, blood volume levels are read to the subject so the subject can determine whether the subject should increase hydration and/or salt intake in order to reduce CBF instability. In some embodiments, the local base station further comprises an acoustic transducer for broadcasting audio messages. In some embodiments, the biometric feedback or behavioral coaching recommendations are delivered via the acoustic transducer of the local base station in the form of one or more audio messages. In some embodiments, the local base station further comprises a screen for displaying biometric information and notifications. In some embodiments, the biometric feedback or behavioral coaching recommendations are delivered via the screen of the local base station in the form of one or more visual messages. In some embodiments, the biometric feedback or behavioral coaching recommendations are delivered to the subject or a caretaker for the subject via text message to a mobile device. In some embodiments, the analysis comprises applying one or more artificial neural networks (ANNs). In some embodiments, the one or more ANNs are configured to detect or predict poor cerebral blood flow, poor blood pressure, presyncope, syncope, and a fall event.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Provided herein are methods, devices, systems, and platforms for detecting Cerebral Blood Flow (CBF) in real-time to prevent dizziness, fainting, and falls.

Technological solutions to helping with falling in the elderly have thus far been focused on fall detection, but fall detection is too late as the damage is already done. Rather than doing just fall detection, the methods described herein are focused on fall prevention through in-the-moment alerts made possible through continuously monitoring Cerebral Blood Flow.

Method of Preventing Presyncope, Syncope and Falls in a Subject

Provided herein is an exemplary method of preventing presyncope, syncope and falls in a subject comprising: receiving biometric data for the subject; aggregating and processing the biometric data; analyzing the data to detect or predict one or more of: poor cerebral blood flow, poor blood pressure, presyncope, syncope, and a fall event; and delivering one or more real-time messages to the subject pertaining to the identified detected or predicted event.

In some embodiments, the biometric data comprises one or more of: cerebral blood flow, blood pressure, blood volume, heart rate, heart rate variability, and blood oxygenation. In some embodiments, the biometric data is generated by a wearable device associated with the subject. In some embodiments, activity data is collected and comprises one or more of: motion, posture, change in posture, activity level, and type of activity. In some embodiments, the activity data is generated by a wearable device associated with the subject.

In some embodiments, analyzing the data comprises applying one or more artificial neural networks (ANNs). In some embodiments, analyzing the data comprises determining a posture or change in posture of the subject. In some embodiments, analyzing the data comprises one or more of: identifying trends pertaining to the biometric data of the subject, identifying trends pertaining to the activity data of the subject, identifying trends pertaining to detected or predicted poor cerebral blood flow of the subject, identifying trends pertaining to detected or predicated presyncope for the subject, identifying trends pertaining to detected or predicted syncope events for the subject, identifying trends pertaining to detected or predicted fall events for the subject. In some embodiments, the poor cerebral blood flow or fall risk threshold is based, at least in part, on one or more of: the biometric data of the subject, the activity data of the subject, demographic information of the subject, and a medical history of the subject. In some embodiments, trends are determined pertaining to the biometric data of the subject by comparing the biometric data with known medical patterns.

In some embodiments, trends are determined by analyzing a blood pressure vs time graph of the biometric data.

Figure 8:
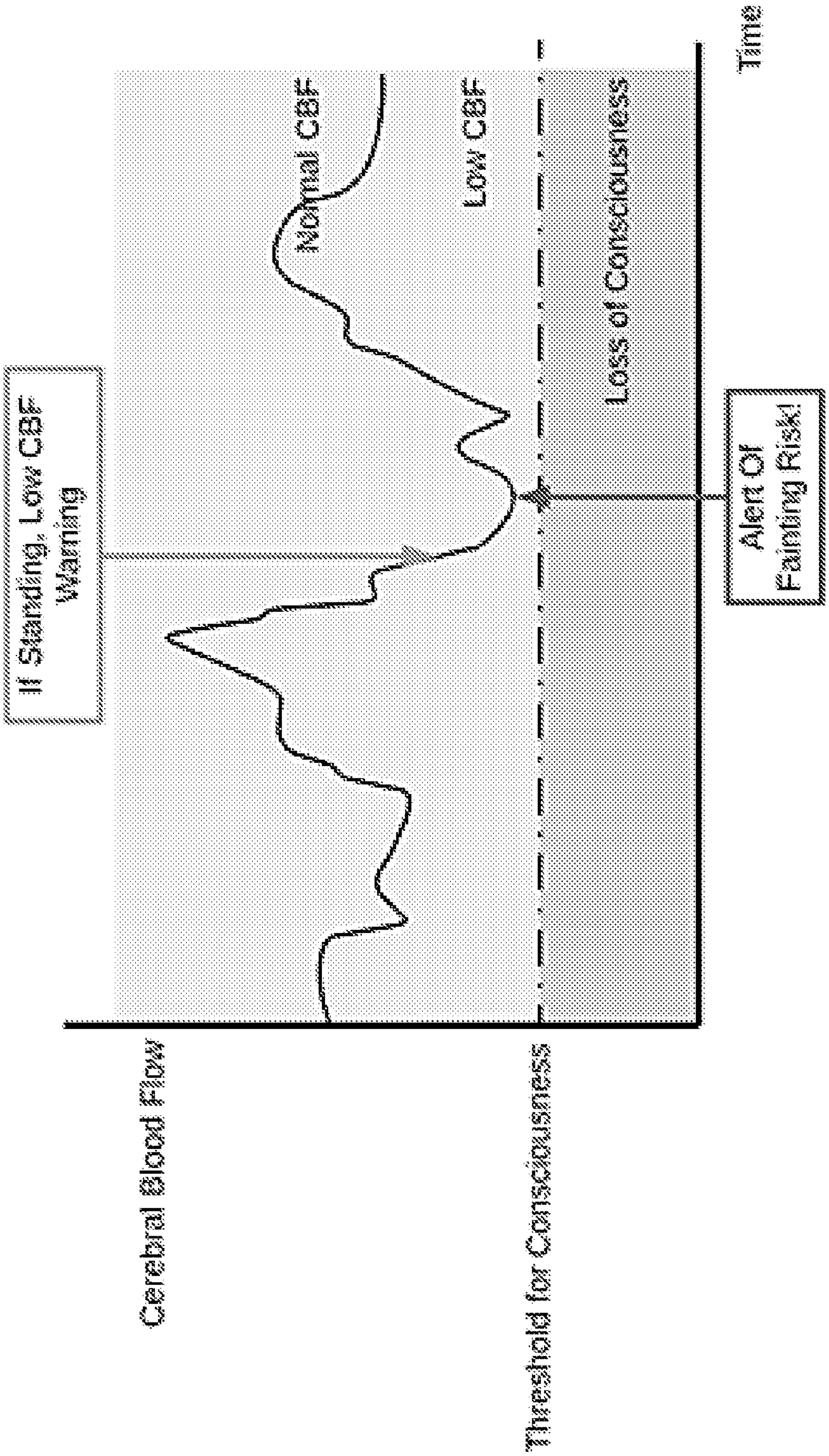
FIG. 8 shows a cerebral blood flow vs time graph with consciousness warnings and alerts; per an embodiment herein.
Figure 9:
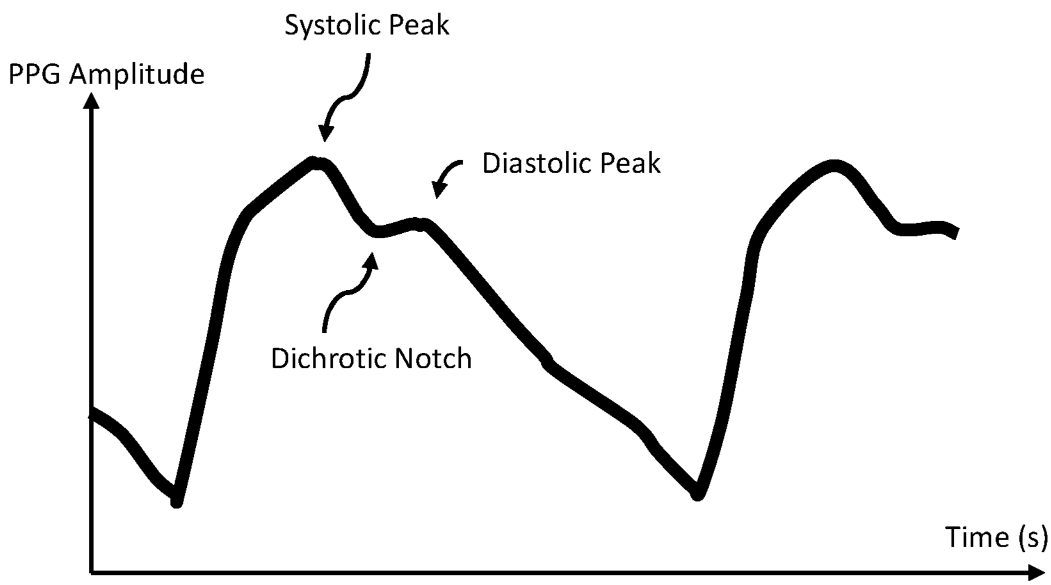
FIG. 9 shows a PPG measured amplitude vs time graph with labeled inflection systolic peak, dichrotic notch, and diastolic peak points; per an embodiment herein.
Figure 10:
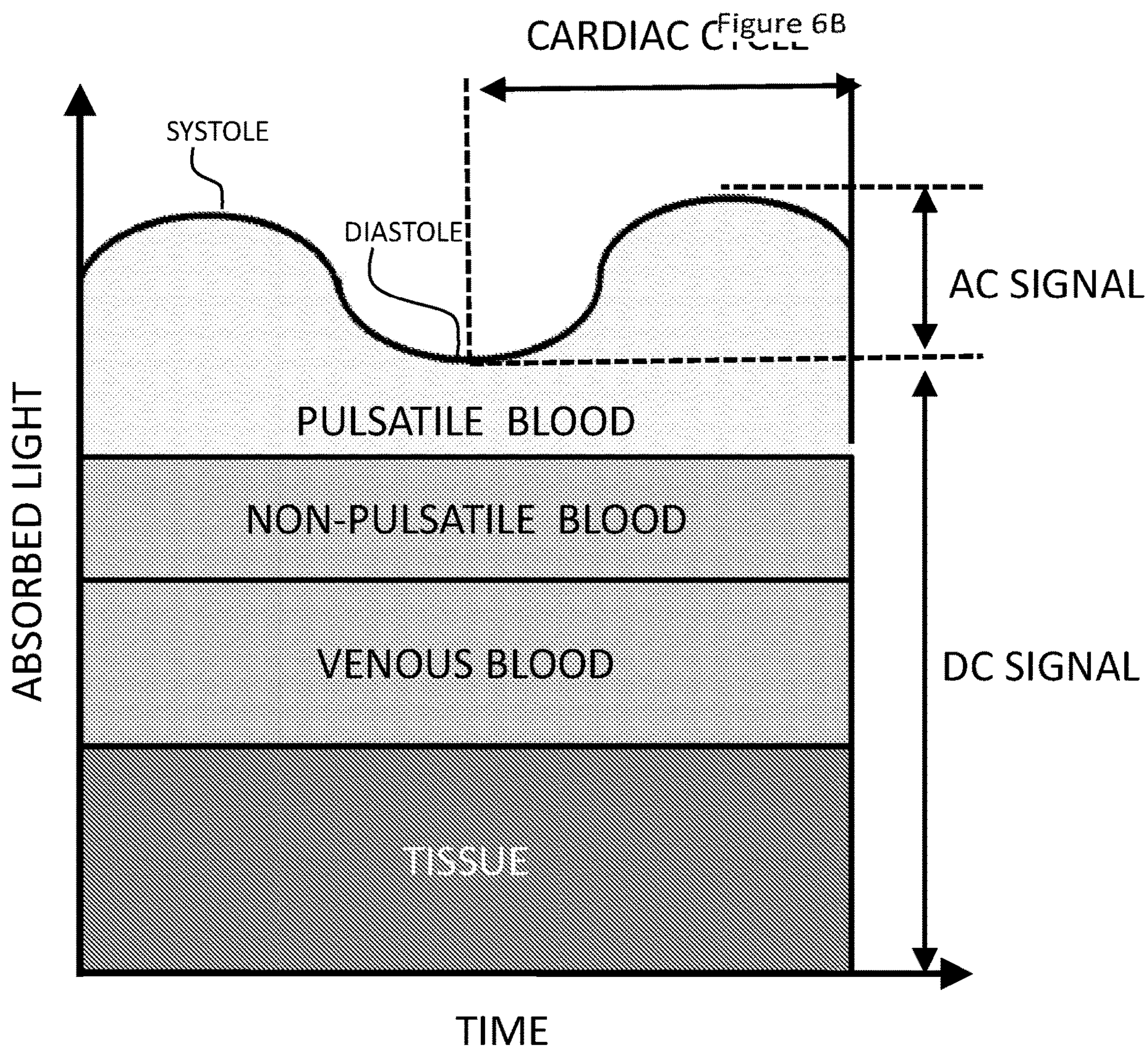
FIG. 10 shows a graph of absorption of the skin and corresponding DC and AC levels; per an embodiment herein

FIG. 8 shows a cerebral blood flow vs time graph that demarcates a consciousness threshold and corresponding user warnings and alerts.

Figure 14:
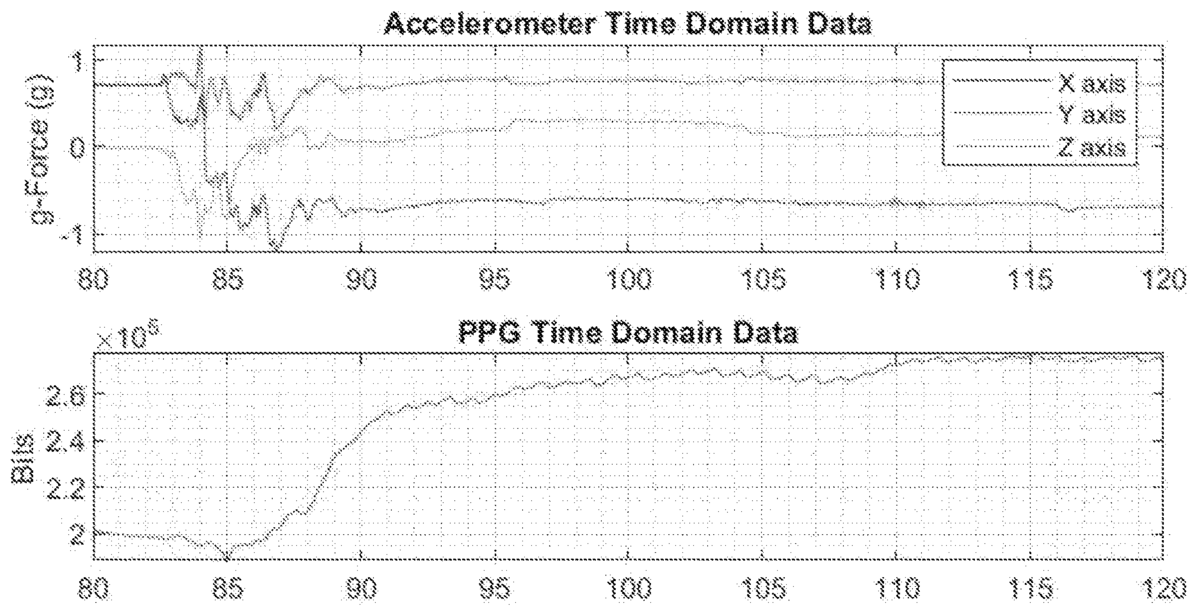
FIG. 14 shows a PPG Amplitude value read by a green light emitting diode (LED) during a transition of an elderly person from a supine to standing position; per an embodiment herein.
Figure 15:
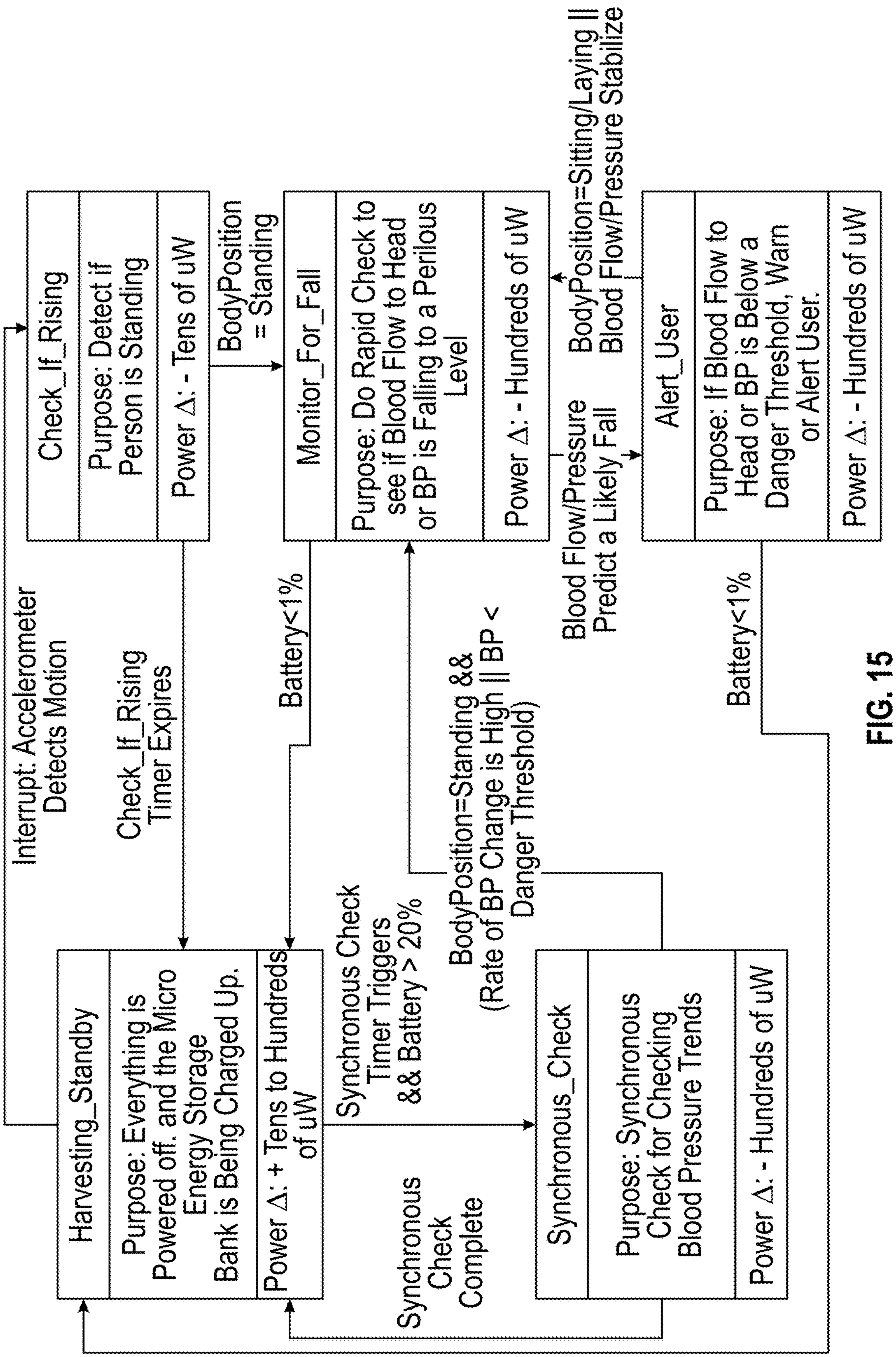
FIG. 15 shows another flowchart of the energy and data transfer in an exemplary in-ear system; per an embodiment herein.

In some embodiments, trends are determined by looking at the changes in cerebral blood flow upon postural changes. FIG. 14 shows a PPG amplitude value read by a green light emitting diode (LED), which reflects the relative level of blood flowing to the sensor location over a 40 second window. This was taken as an elderly subject transitioned from a supine to a standing position. The accelerometer data is provided to demarcate the timing of the postural change. You can see the dramatic change in cerebral blood flow as a result of the postural change. Younger healthy subjects do not exhibit as dramatic changes due to more elastic vasculature and better baroreceptor reflex function, amongst other age-related dynamics.

In some embodiments, the one or more real-time messages comprise an audio message delivered utilizing an acoustic transducer configured to deliver audio messages into the ear of the subject. In some embodiments, the device is configured to operate as an open ear audio device, and wherein the audio messages are delivered to the subject with low sound leakage perceived by others near the subject. In some embodiments, the method further comprises determining one or more applicable audio messages for the subject. In some embodiments, the one or more applicable audio messages for the subject comprise biometric feedback, a behavioral coaching recommendation, a warning, or an alert. In some embodiments, the biometric feedback or behavioral coaching recommendation may be conducted by reading to the subject one or more of their biometric parameters measured in that moment. In some embodiments, relative CBF percentage changes are read to the subject in real-time so the subject can determine if/when they should take action to avoid fainting. In some embodiments, blood volume levels are read to the subject so the subject can determine whether the subject should increase hydration and/or salt intake in order to reduce CBF instability.

Figure 7:
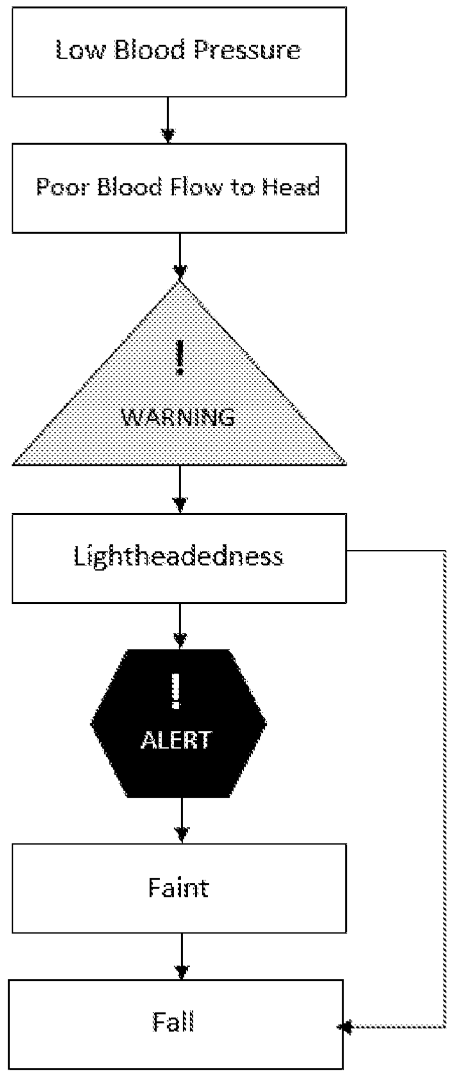
FIG. 7 shows an exemplary treatment method of in-the-moment warnings and alerts made possible through continuous monitoring of cerebral blood flow; per an embodiment herein.

FIG. 7 shows a treatment method of in-the-moment warnings and alerts made possible through continuous monitoring of cerebral blood flow. In some embodiments, the method comprises conveying the audio message in real-time. In some embodiments, the method comprises conveying the audio message in real-time, such that a period of time between the measurement of the sensor data, and the conveying of the audio message is at most about 1 microsecond, 5 microseconds, 10 microseconds, 50 microseconds, 100 microseconds, 500 microseconds, 1 millisecond, 5 millisecond, 10 millisecond, 50 millisecond, 100 millisecond, 500 millisecond, 1 second, 5 seconds, 10 seconds, or 50 seconds including increments therein. In some embodiments, as poor cerebral blood flow, poor blood pressure, presyncope, syncope, and fall events can develop quickly (e.g. within seconds) aggregating and processing the sensor data, detecting or predicting the event, and conveying the audio message in real-time greatly improves the odds of alerting the subject and/or a caretaker in time to prevent the event or further harm.

In some embodiments, the system provides intraday and interday interventions. In some embodiments, the intraday interventions, the interday interventions, or both are provided in an audio notification or alert, a visual notification or alert, a text notification, or any combination thereof. In some embodiments, the intraday intervention comprise a daily blood pressure readout, cerebral blood flow readout, high fall risk alert, fall detection alert, a caretaker notification or any combination thereof. Examples of interday user interventions are historical dashboards, trends, lifestyle tips, and disease detections.

Figure 6:
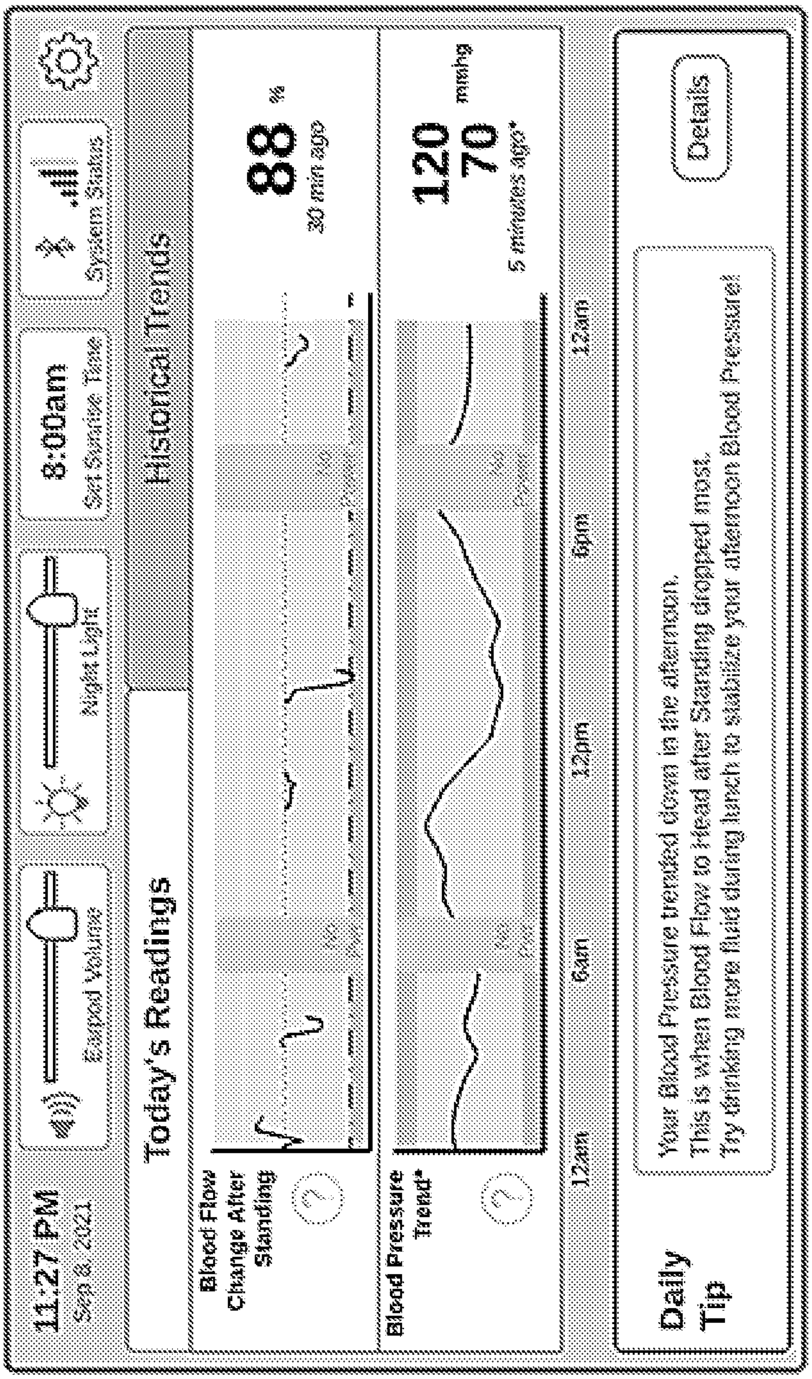
FIG. 6 shows an illustration of an exemplary graphical user interface (GUI) for displaying intraday cerebral blood flow changes, blood pressure, heart rate, and blood oxygenation by an in-ear device mechanism; per an embodiment herein.

In some embodiments, the one or more real-time messages comprise a visual message delivered utilizing a display of a device of the subject or a caretaker of the subject. In some embodiments, the method further comprises determining one or more applicable visual messages for the subject. In some embodiments, the one or more applicable visual messages for the subject comprise biometric feedback, a behavioral coaching recommendation, an alert, or a warning. In some embodiments, the method further comprises providing a subject health portal application allowing access to real-time and historical biometric data and activity data and trends for the subject. In some embodiments, the method further comprises providing a healthcare provider portal application allowing access to real-time and historical biometric data and activity data and trends for one or more subjects. FIG. 6 shows an illustration of an exemplary graphical user interface (GUI) for displaying intraday cerebral blood flow changes, blood pressure, heart rate, and blood oxygenation by an in-ear device.

Wearable Device for Preventing Presyncope, Syncope and Falls

Provided herein, per FIGS. 1-4 are exemplary wearable devices 100 for preventing presyncope, syncope and falls. In some embodiments, the device 100 comprises a biometric sensor 101, a movement sensor 102, a logic element 103, an acoustic transducer 104, a wireless communications transceiver 105, and a microcontroller 106. In some embodiments, the device 100 further comprises a housing containing the biometric sensor 101, the movement sensor 102, the logic element 103, the acoustic transducer 104, the wireless communications transceiver 105, the microcontroller 106, or any combination thereof. In some embodiments, the device 100 is configured to operate as an open ear audio device 100. In some embodiments, device 100 is configured to deliver audio messages to the subject with low sound leakage perceived by others near the subject. In some embodiments, the device 100 is configured to deliver the audio messages in real-time.

In some embodiments, the acoustic transducer 104 is configured to deliver audio messages into the ear of the subject. In some embodiments, the acoustic transducer 104 enables the device 100 to operate as an open ear audio device 100. In some embodiments, the acoustic transducer 104 delivers audio messages to the ear of the subject while at least a portion of the ear canal of the subject is unobstructed. In some embodiments, the acoustic transducer 104 delivers audio messages to the ear of the subject while the entire ear canal of the subject is unobstructed. In some embodiments, the entire device 100 is configured to be positioned outside the ear canal of the subject during delivery of the audio message. In some embodiments, maintaining an unobstructed ear canal enables the device 100 to be used without compromising the hearing of the subject.

In some embodiments, the acoustic transducer 104 enables the device 100 to operate with low sound leakage perceived by others near the subject, enabled by the acoustic transducer's close proximity to the subject's ear canal resulting in acoustics similar to that of whispering in someone's ear. In some embodiments, the acoustic transducer 104 emits the audio message at a volume such that a subject (e.g. a subject without significant hearing disabilities) can hear and understand the audio message. In some embodiments, the acoustic transducer 104 emits the audio message at a frequency such that a subject (e.g. a subject without hearing disabilities) can hear and understand the audio message. In some embodiments, the acoustic transducer 104 emits the audio message at a volume such that another person (e.g. a person without hearing disabilities) within about 1, 2, 3, 4, 5, 6, 7, 8, 9, 10 or more feet from the subject is not able to hear or understand the audio message. In some embodiments, the acoustic transducer 104 emits the audio message at a frequency such that another person (e.g. a person without hearing disabilities) within about 1, 2, 3, 4, 5, 6, 7, 8, 9, 10 or more feet from the subject is not able to hear or understand the audio message. In some embodiments, the audio messages comprise one or more of: biometric feedback, a behavioral coaching recommendation, a warning, and an alert pertaining to one or more of: poor cerebral blood flow, poor blood pressure, presyncope, syncope, and a fall event. In some embodiments, the audio messages comprise a speech-based instruction regarding one or more of: biometric feedback, the behavioral coaching recommendation, the warning, and the alert pertaining to one or more of: poor cerebral blood flow, poor blood pressure, risk of syncope, and risk of falling. In some embodiments, the audio messages comprise an alarm or chime regarding one or more of: biometric feedback, the behavioral coaching recommendation, the warning, and the alert pertaining to one or more of: poor cerebral blood flow, poor blood pressure, risk of syncope, risk of falling.

In some embodiments, the biometric sensor 101 is configured to monitor at least one biometric parameter of the subject. In some embodiments, the biometric sensor 101 comprises an optical sensor. In some embodiments, the optical sensor comprises a photoplethysmography (PPG) sensor. In some embodiments, the at least one biometric parameter of the subject comprises one or more of: cerebral blood flow, blood pressure, blood volume, heart rate, heart rate variability, or blood oxygenation. In some embodiments, the wearable device 100 further comprises a temperature sensor. In some embodiments, the at least one biometric parameter of the subject comprises temperature.

In some embodiments, the movement sensor 102 is configured to monitor at least one activity parameter of the subject. In some embodiments, the movement sensor 102 comprises at least one accelerometer. In some embodiments, the at least one activity parameter of the subject comprises an activity level. In some embodiments, the activity level is associated with a movement frequency of movement sensor 102, a velocity of movement sensor 102, an acceleration of the movement sensor 102, or any combination thereof. In some embodiments, the activity level is associated with a relative movement frequency between two or more movement sensors 102, a relative velocity of movement between two or more movement sensors 102, a relative acceleration of the movement sensor 102 between two or more movement sensors 102, or any combination thereof.

In some embodiments, the microcontroller 106 is configured to aggregate and process sensor data. In some embodiments, the microcontroller 106 is configured to pass processed data to the wireless communications transceiver 105. In some embodiments, the microcontroller 106 is further configured to analyze the data to detect or predict one or more of: poor cerebral blood flow, poor blood pressure, presyncope, syncope, and a fall event. In some embodiments, the change in posture is sitting up from a laying posture, standing from a sitting posture, standing from a kneeling posture, standing from a squatting posture, or standing upright from a bent standing posture. In some embodiments, the microcontroller 106 is configured to determine an audio message content based on the processed data, the detected or predicted presyncope event, the detected or predicted syncope, the detected or predicted fall event, or any combination thereof. In some embodiments, a neural net model determines a cerebral blood flow metric, sitting blood pressure, a standing blood pressure, a laying blood pressure, a hypertension classification, an orthostatic hypotension classification, a user dizziness score, a syncope risk score, or any combination thereof.

In some embodiments, the microcontroller 106 is configured to aggregate and process sensor data, detect or predict an event, and direct the acoustic transducer 104 to convey the audio message in real-time. In some embodiments, the microcontroller 106 is configured to aggregate and process sensor data, detect or predict an event, and direct the acoustic transducer 104 to convey the audio message in real-time, such that a period of time between the measurement of the sensor data, and the conveying of the audio message by the acoustic transducer 104 is at most about 1 millisecond, 5 millisecond, 10 millisecond, 50 millisecond, 100 millisecond, 500 millisecond, 1 second, 5 seconds, 10 seconds, or 50 seconds including increments therein. In some embodiments, as poor cerebral blood flow, poor blood pressure, presyncope, syncope, and fall events can develop quickly (e.g. within seconds), aggregating and processing the sensor data, detecting or predicting the event, and directing the acoustic transducer 104 to convey the audio message in real-time greatly improves the odds of alerting the subject and/or a caretaker in time to prevent the event or further harm.

In some embodiments, the microcontroller 106 is further configured to provide a visual message based on the detection and/or prediction of poor cerebral blood flow, poor blood pressure, presyncope, syncope, a fall event, or any combination thereof. In some embodiments, the microcontroller 106 controls a user interface to display the visual message. In some embodiments, the microcontroller utilizes the wireless communications transceiver 105 to communicate with an external device 108 that provides the user interface medium through which the visual message is delivered.

In some embodiments, the logic element 103 performs state management. In some embodiments, the state management enables a sleep state, a first wake state, or a second wake state of the device 100. In some embodiments, in the first wake state, the second wake state, or both, the device 100 performs synchronous monitoring of the subject. In some embodiments, the state management maintains the device 100 in a sleep state, shifts the device 100 to the first wake state intermittently, at a predefined interval, and shifts the device 100 to a second wake state. In some embodiments, the state management shifts the device 100 to the second wake state when the at least one activity parameter indicates a change in posture of the subject. In some embodiments, in the sleep state, the micro energy storage bank is charged. In some embodiments, in the first wake state and the second wake state, the micro energy storage bank powers operation of the biometric sensor 101, the movement sensor 102, the acoustic transducer 104, and the wireless communications transceiver 105. In some embodiments, the predefined interval is between about 1 minute to about 30 minutes. In some embodiments, the state management further comprises returning the device 100 to the sleep state after performing the synchronous or asynchronous monitoring of the subject for a monitoring period. In some embodiments, the monitoring period is between about 5 seconds to about 120 seconds. In some embodiments, in the first wake state or the second wake state, the biometric sensor 101 monitors the at least one biometric parameter of the subject at a rate of between about 1 Hz to about 200 Hz. In some embodiments, in the first wake state or the second wake state, the movement sensor 102 monitors the at least one activity parameter of the subject at a rate of between about 1 Hz to about 200 Hz.

In some embodiments, the wireless communications transceiver 105 utilizes a Near-Field Communication (NFC) protocol, Bluetooth, Bluetooth Low Energy, LoRa, or Wi-Fi. In some embodiments, the wireless communications transceiver 105 is configured to send data to an external device 108 and receive data from the external device 108. In some embodiments, the external device 108 comprises a local base station, a mobile device of the subject, or at least one server.

In some embodiments, the wearable device 100 further comprises a micro energy storage bank. In some embodiments, the micro energy storage bank comprises a supercapacitor or a micro battery. In some embodiments, the micro energy storage bank has a maximum capacity of no more than 10 milli-Watt-hour (mWh). In some embodiments, the wearable device 100 further comprises an energy harvesting element configured to charge the micro energy storage bank. In some embodiments, the energy harvesting element comprises a photovoltaic cell configured to harvest energy from natural daylight, interior lighting, and infrared emitters. In some embodiments, the energy harvesting element comprises a RF antenna configured to harvest energy from the environment of the device 100. In some embodiments, the energy harvesting element comprises a thermoelectric generator configured to harvest energy from body heat of the subject. In some embodiments, the energy harvesting element comprises a piezoelectric material configured to harvest energy from motion of the subject. In some embodiments, a charging and/or discharging state of the device 100 is configured to optimize energy harvesting and energy usage periods.

Figure 1:
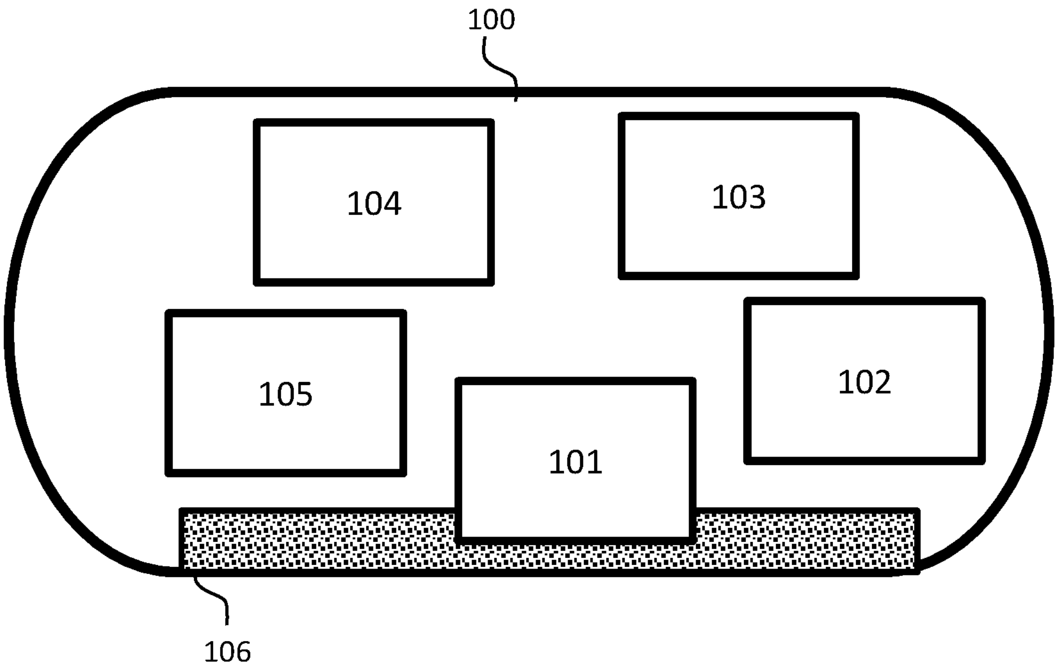
FIG. 1 shows a diagram of the components of an exemplary in-ear device; per an embodiment herein.
Figure 2:
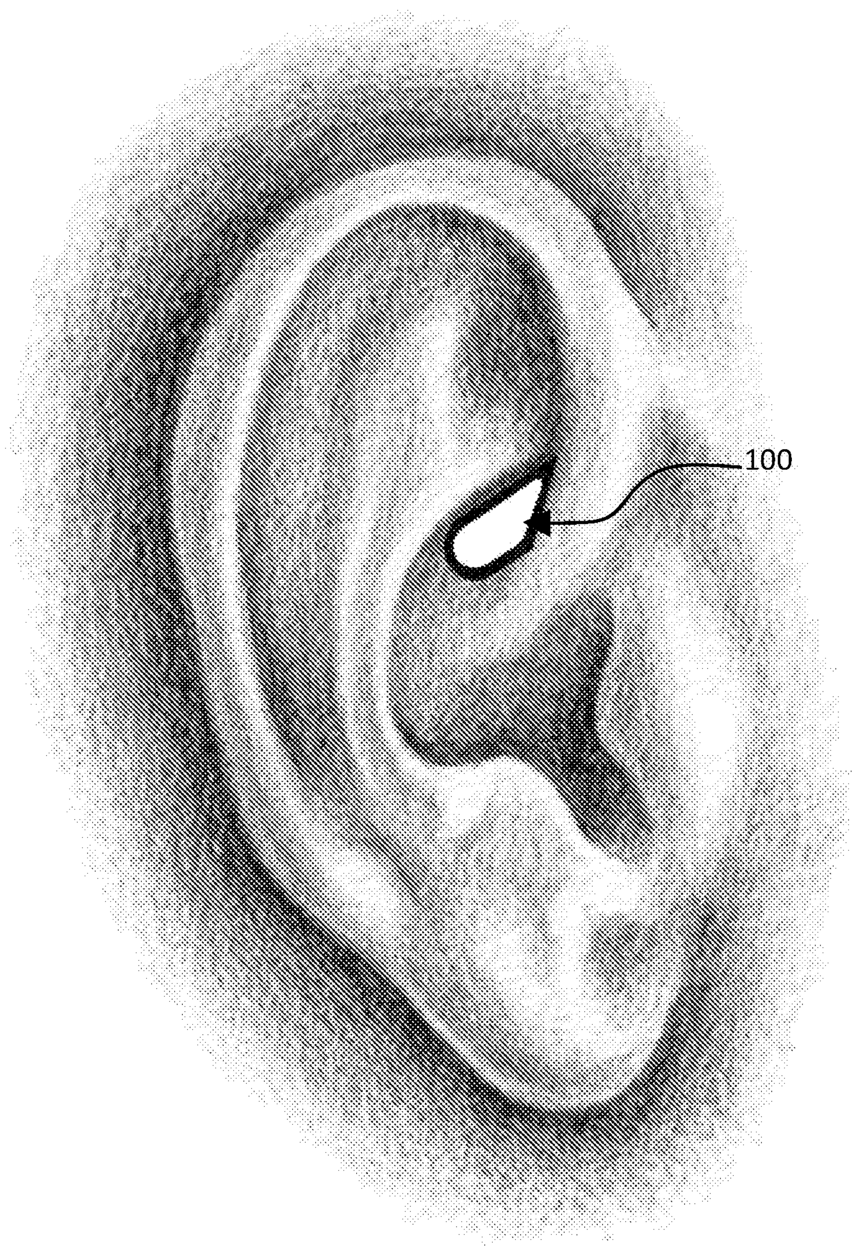
FIG. 2 shows an illustration of an exemplary in-ear device; per an embodiment herein.
Figure 4A:
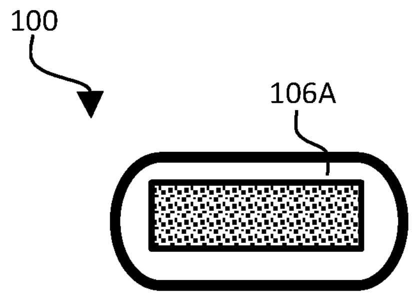
FIG. 4A shows an illustration of an exemplary in-ear device with a first attachment mechanism; per an embodiment herein.
Figure 4B:
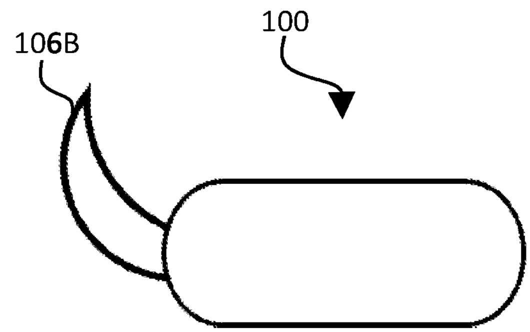
FIG. 4B shows an illustration of an exemplary in-ear device with a second attachment mechanism; per an embodiment herein.
Figure 4C:
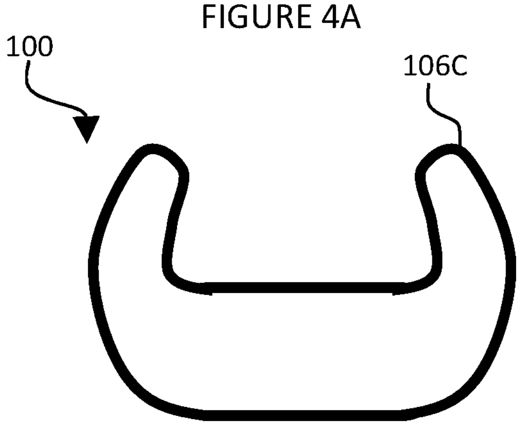
FIG. 4C shows an illustration of an exemplary in-ear device with a third attachment mechanism; per an embodiment herein.
Figure 4D:
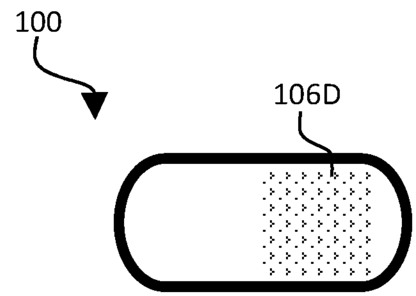
FIG. 4D shows an illustration of an exemplary in-ear device with a fourth attachment mechanism; per an embodiment herein.
Figure 4E:
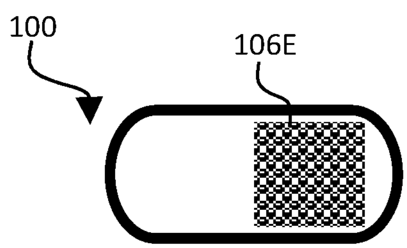
FIG. 4E shows an illustration of an exemplary in-ear device with a fifth attachment mechanism; per an embodiment herein.
Figure 4F:
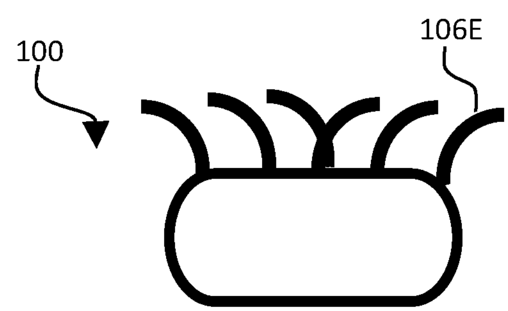
FIG. 4F shows an illustration of an exemplary in-ear device with a sixth attachment mechanism; per an embodiment herein.
Figure 4G:
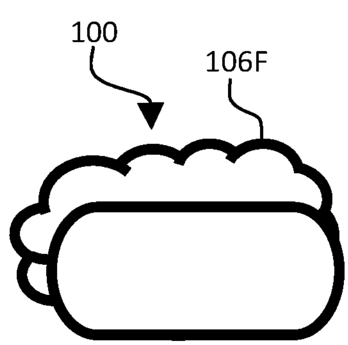
FIG. 4G shows an illustration of an exemplary in-ear device with a seventh attachment mechanism; per an embodiment herein.

In some embodiments, per FIGS. 1 and 4A, the wearable device 100 further comprises an attachment mechanism for attaching the device 100 to the subject. In some embodiments, the device 100 is adapted to attach to an auricle of the subject. In some embodiments, the device 100 is adapted to attach to the auricle of the subject at the cymba concha, scapha, triangular fossa, anti-helix, or inner surface of the helix of the subject. In some embodiments, the device 100 is adapted to attach to the auricle of the subject at the cymba concha of the subject.

Figure 3:
FIG. 3 shows an image of an exemplary in-ear device; per an embodiment herein.

In some embodiments, the one or more biometric sensors targets the Cymba Concha, enabling excellent signal quality due to proximity to branches of the Posterior Auricular Artery. In some embodiments, the posterior auricular artery climbs up the back of the ear, perforates through the ear cartilage to the front of the ear, and travels across the Cymba Concha. In some embodiments, the biometric sensors herein target this branch of the posterior auricular artery for improved sensing. In some embodiments, targeting this branch of the posterior auricular artery increases photoplethysmography (PPG) quality In some embodiments, per FIG. 4B, the attachment mechanism 106 comprises one or more elastomeric wings 106B. A device 100 comprising the elastomeric wings 106B is shown in FIG. 3. In some embodiments, per FIG. 4C, the attachment mechanism 106 is one or more elastomeric clips 106C. In some embodiments, per FIG. 4D, the attachment mechanism 106 is one or more elastomeric rough surface finishes 106D. In some embodiments, per FIG. 4E, the attachment mechanism 106 is one or more elastomeric suction cups 106E. In some embodiments, per FIG. 4F, the attachment mechanism 106 is a set of elastomeric appendages 106E. In some embodiments, per FIG. 4G, the attachment mechanism 106 is an elastomeric mold 106F.

In some embodiments, the device 100 has a longest dimension of at most about 15 mm. In some embodiments, the device 100 has a longest dimension of at most about 12 mm. In some embodiments, the small size of the device 100 enables its use in the auricle of the subject while maintaining an open ear canal of the patient.

System for Preventing Presyncope, Syncope and Falls in a Subject

Another aspect provided herein is a system for preventing presyncope, syncope and falls in a subject. In some embodiments, the system comprises the wearable device as described in any one or more embodiment herein, and a local base station.

In some embodiments, the local base station comprises a wireless communications transceiver and a network interface. In some embodiments, the wireless communications transceiver is configured to send data to the wearable device, receive data from wearable device, or both. In some embodiments, the network interface is configured to provide connectivity to a computer network. In some embodiments, the local base station further comprises a wireless power transmitter (WPT) comprising an RF energy transmission antenna. In some embodiments, the local base station further comprises a wireless power transmitter (WPT) comprising infrared light emitters. In some embodiments, the infrared light emitters comprise infrared light-emitting diodes (LEDs). In some embodiments, the local base station further comprises an acoustic transducer for broadcasting audio messages. In some embodiments, the local base station further comprises a screen for displaying biometric information and notifications. In some embodiments, the wearable device further comprises an attachment mechanism for attaching the device to an auricle of the subject. In some embodiments, the local base station further comprises one or more processors configured to transmit an alert via one or more of: SMS, MMS, email, telephone, voice mail, and social media. In some embodiments, the computer network comprises the internet.

Figure 5:
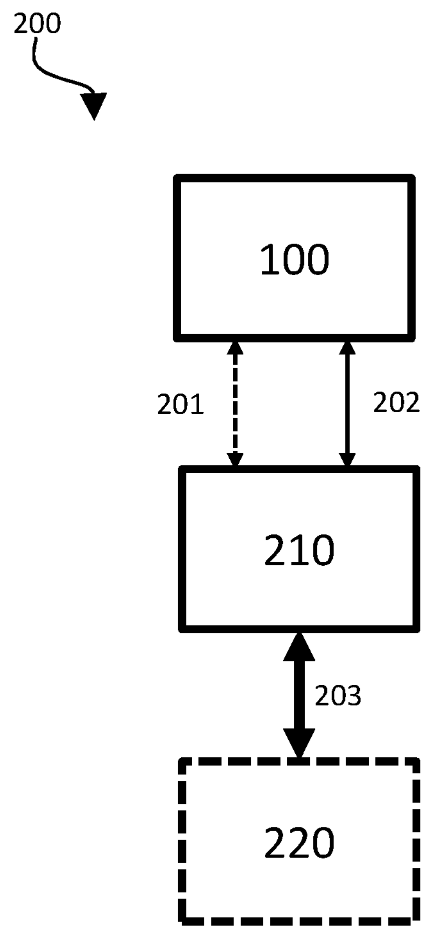
FIG. 5 shows a flowchart of the energy and data transfer in an exemplary in-ear system; per an embodiment herein.

In some embodiments, the local base station 210 comprises a wireless communications transceiver and a network 220 interface. In some embodiments, per FIG. 5., the wireless communication transceiver is configured to send a first data 201 to the in-ear device 100 and receive a first data 201 from the in-ear device 100. In some embodiments, the network interface is configured to provide connectivity to a computer network 220. In some embodiments, the network interface is configured to transmit a second data 203 to the computer network 220. In some embodiments, the first data 201, the second data 203, or both comprise the biometric parameter, the activity parameter, or both. In some embodiments, the first data 201, the second data 203, or both are based on the biometric parameter, the activity parameter, or both. In some embodiments, a transmission/reception bandwidth of the second data 203 is greater than a transmission/reception bandwidth of the first data 201. In some embodiments, power provided to the local base station 210 by a battery or a wall outlet enables the transmission/reception bandwidth of the second data 203 to be greater than a transmission/reception bandwidth of the first data 201. In some embodiments, the difference between the transmission/reception bandwidth of the second data 203 and the first data 201 reduces the power required by the in-ear device 100 to communicate with the computer network 220. In some embodiments, the physiological trends comprise intraday and interday trends of cerebral blood flow, blood pressure, presyncope risk, syncope risk, and fall risk.

Platforms for Predicting Presyncope, Syncope and Fall Events in a Subject

Another aspect provided herein is a platform for predicting presyncope, syncope and fall events in a subject. In some embodiments, the platform comprises the wearable device, as described in any one or more embodiment herein, the local base station, as described in any one or more embodiment herein, and a cloud computing back-end.

In some embodiments, the network interface is configured to provide connectivity to the cloud computing back-end; and a cloud computing back-end comprising: a module configured to store and analyze the biometric and activity data of the subject to identify trends and provide resulting biometric feedback and behavioral coaching recommendations; and a module configured to determine one or more applicable audio messages for the subject. In some embodiments, the computer network comprises the internet. In some embodiments, the analysis comprises one or more of: identifying trends pertaining to the biometric data of the subject, identifying trends pertaining to the activity data of the subject, identifying trends pertaining to cerebral blood flow for the subject, identifying trends pertaining to predicted or actual presyncope events for the subject, identifying trends pertaining to predicted or actual syncope events for the subject, or identifying trends pertaining to predicted or actual fall events for the subject. In some embodiments, the analysis is further based on an age, gender, height, weight, existing diagnoses, comorbid conditions, number of previous falls, medication, or any combination thereof of the subject. In some embodiments, the analysis receives user data via a user survey. In some embodiments, the user survey conducts a question and response that collects age, gender, height, weight, existing diagnoses, comorbid conditions, number of previous falls, medications, or any combination thereof.

Figure 16:
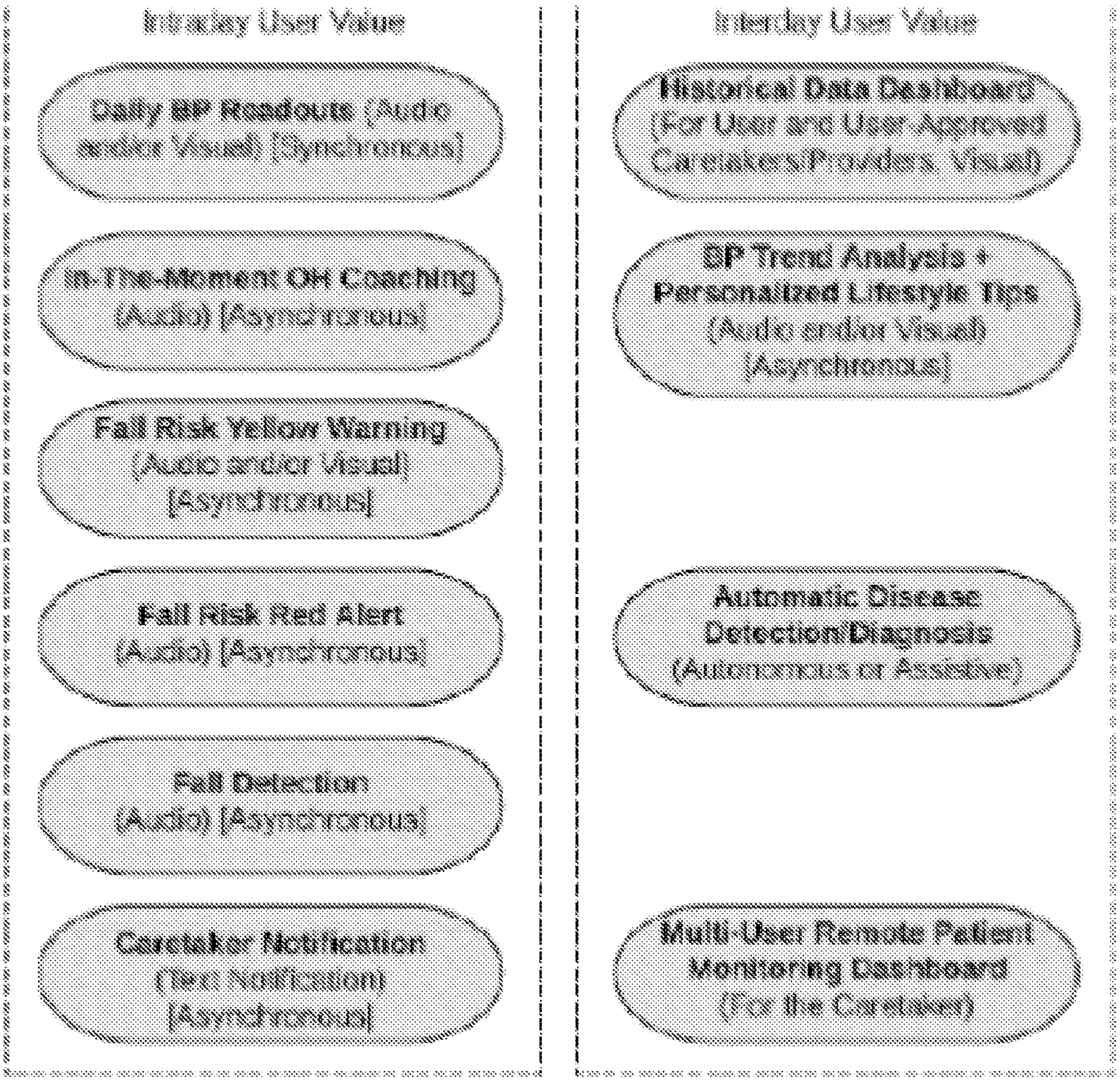
FIG. 16 shows a list of exemplary potential user features that provide value to a caregiver or user, per an embodiment herein.

FIG. 16 shows a list of exemplary user properties that provide value to a caregiver or the user. In some embodiments, the cloud computing back-end further comprises a module configured to provide a healthcare provider portal application allowing access to real-time and historical data and trends for one or more subjects. In some embodiments, the cloud computing back-end further comprises a module configured to provide a subject health portal application allowing access to real-time and historical data and trends for the subject. In some embodiments, the biometric feedback or behavioral coaching recommendations pertain to prevention of poor cerebral blood flow, poor blood pressure, presyncope, syncope that may result in a fall. In some embodiments, the biometric feedback or behavioral coaching recommendations are delivered to the subject via the acoustic transducer in the form of one or more audio messages. In some embodiments, the local base station further comprises an acoustic transducer for broadcasting audio messages. In some embodiments, the biometric feedback or behavioral coaching recommendations are delivered via an acoustic transducer in the local base station in the form of one or more audio messages. In some embodiments, the local base station further comprises a screen for displaying biometric information and notifications. In some embodiments, the biometric feedback or behavioral coaching recommendations are delivered via the screen of the local base station in the form of one or more visual messages. In some embodiments, the biometric feedback or behavioral coaching recommendations are delivered to the subject or a caretaker for the subject via text message to a mobile device. In some embodiments, the analysis comprises applying one or more artificial neural networks (ANNs). In some embodiments, the one or more ANNs are configured to detect or predict poor cerebral blood flow, poor blood pressure, presyncope, syncope, and a fall event.

Machine Learning

In some embodiments, machine learning algorithms are utilized to process the biometric data and the activity data. In some embodiments, the machine learning algorithm is used to analyze the data to detect or predict one or more of: poor cerebral blood flow, poor blood pressure, presyncope, syncope, and a fall event. In some embodiments, the machine learning algorithm is used to identify one or more of the detected or predicted events. In some embodiments, an ANN model outputs a cerebral blood flow metric, a sitting blood pressure, a standing blood pressure, a laying blood pressure, a hypertension classification, an orthostatic hypotension classification, a user dizziness score, a syncope risk score, or any combination thereof.

In some embodiments, the machine learning algorithms utilized herein employ one or more forms of labels including but not limited to human annotated labels and semi-supervised labels. The human annotated labels can be provided by a hand-crafted heuristic. For example, the hand-crafted heuristic can comprise comparing a current blood pressure to a predetermined blood pressure graph. The semi-supervised labels can be determined using a clustering technique to determine poor cerebral blood flow, poor blood pressure, presyncope, syncope, or a fall event similar to those flagged by previous human annotated labels and previous semi-supervised labels. The semi-supervised labels can employ a XGBoost, a neural network, or both.

In some embodiments, the methods and systems herein employ a distant supervision method. The distant supervision method can create a large training set seeded by a small hand-annotated training set. The distant supervision method can comprise positive-unlabeled learning with the training set as the 'positive' class. The distant supervision method can employ a logistic regression model, a recurrent neural network, or both.

Examples of machine learning algorithms can include a support vector machine (SVM), a naïve Bayes classification, a random forest, a neural network, deep learning, or other supervised learning algorithm or unsupervised learning algorithm for classification and regression. The machine learning algorithms can be trained using one or more training datasets.

In some embodiments, the machine learning algorithm utilizes regression modeling, wherein relationships between predictor variables and dependent variables are determined and weighted. In one embodiment, for example, a predicted event can be a dependent variable and is derived from the biometric and activity data.

In some embodiments, a machine learning algorithm is used to infer systolic and diastolic blood pressures from the available biometric and user profile data. A non-limiting example of a multi-variate linear regression model algorithm is seen below: probability=$A_0+A_1(X_1)\ A_2(X_2)+A_3(X_3)+A_4(X_4)+A_5(X_5)+A_6(X_6)+A_7(X_7)\ \ldots$ wherein $A_i$ ($A_1$, $A_2$, $A_3$, $A_4$, $A_5$, $A_6$, $A_7$, . . . ) are "weights" or coefficients found during the regression modeling; and $X_i$ ($X_1$, $X_2$, $X_3$, $X_4$, $X_5$, $X_6$, $X_7$, . . . ) are data collected from the Subject. Any number of $A_i$ and $X_i$ variable can be included in the model. For example, in a non-limiting example wherein there are 3 $X_i$ terms, $X_i$ is the biometric data, $X_2$ is the activity data, and $X_3$ is the probability that an event has been detected or predicted. In some embodiments, the programming language "Python" is used to run the model.

In some embodiments, training comprises multiple steps. In a first step, an initial model is constructed by assigning probability weights to predictor variables. In a second step, the initial model is used to infer blood pressure values. In a third step, the validation module compares against labeled blood pressure data and feeds back the verified data to improve prediction accuracy. At least one of the first step, the second step, and the third step can repeat one or more times continuously or at set intervals.

Computing System

Figure 11:
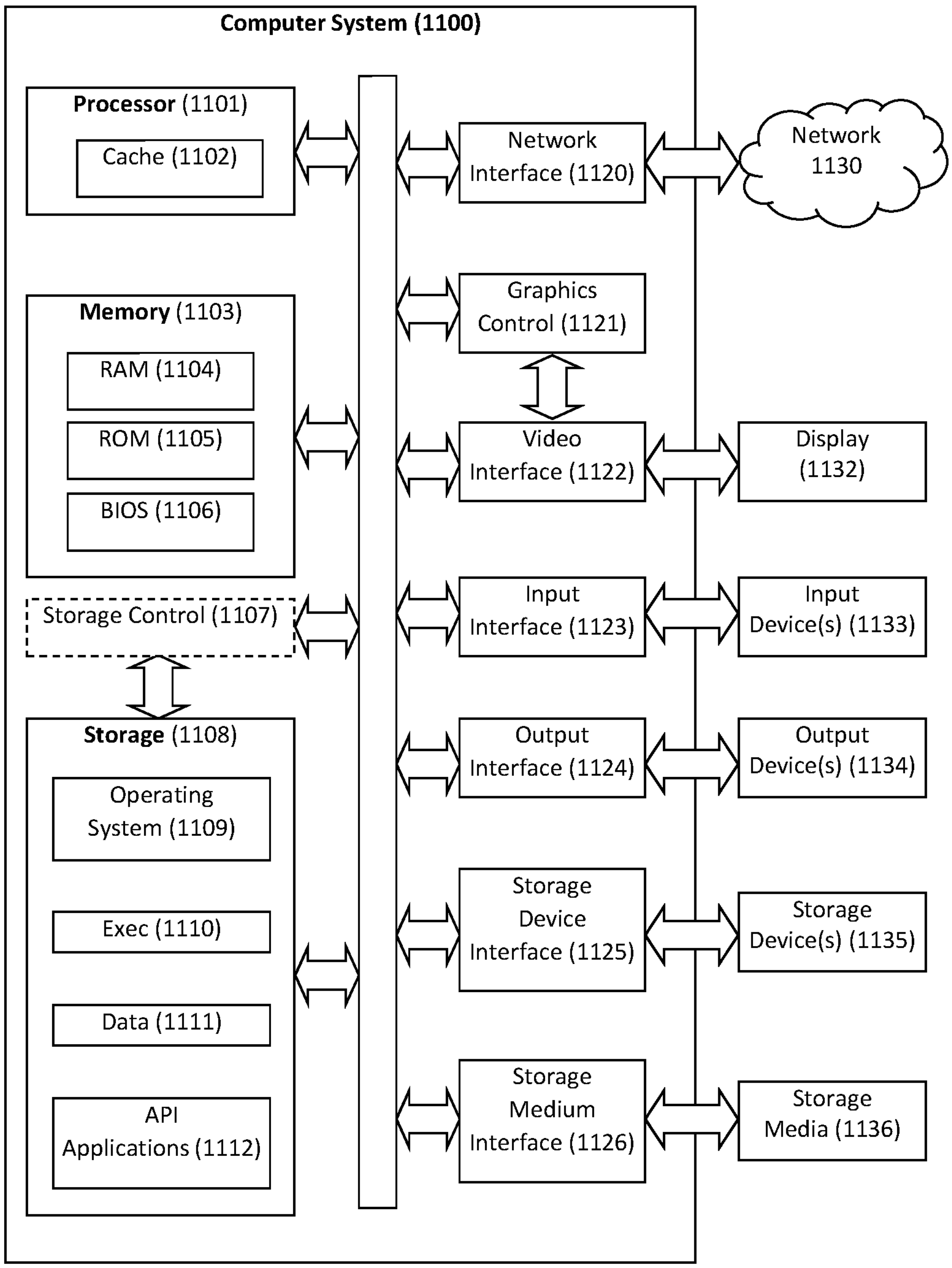
FIG. 11 shows a non-limiting example of a computing device; in this case, a device with one or more processors, memory, storage, and a network interface; per an embodiment herein.

Referring to FIG. 11, a block diagram is shown depicting an exemplary machine that includes a computer system 1100 (e.g., a processing or computing system) within which a set of instructions can execute for causing a device to perform or execute any one or more of the aspects and/or methodologies for static code scheduling of the present disclosure. The components in FIG. 11 are examples only and do not limit the scope of use or functionality of any hardware, software, embedded logic component, or a combination of two or more such components implementing particular embodiments.

Computer system 1100 may include one or more processors 1101, a memory 1103, and a storage 1108 that communicate with each other, and with other components, via a bus 1140. The bus 1140 may also link a display 1132, one or more input devices 1133 (which may, for example, include a keypad, a keyboard, a mouse, a stylus, etc.), one or more output devices 1134, one or more storage devices 1135, and various tangible storage media 1136. All of these elements may interface directly or via one or more interfaces or adaptors to the bus 1140. For instance, the various tangible storage media 1136 can interface with the bus 1140 via storage medium interface 1126. Computer system 1100 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 1100 includes one or more processor(s) 1101 (e.g., central processing units (CPUs) or general purpose graphics processing units (GPGPUs)) that carry out functions. Processor(s) 1101 optionally contains a cache memory unit 1102 for temporary local storage of instructions, data, or computer addresses. Processor(s) 1101 are configured to assist in execution of computer readable instructions. Computer system 1100 may provide functionality for the components depicted in FIG. 11 as a result of the processor(s) 1101 executing non-transitory, processor-executable instructions embodied in one or more tangible computer-readable storage media, such as memory 1103, storage 1108, storage devices 1135, and/or storage medium 1136. The computer-readable media may store software that implements particular embodiments, and processor(s) 1101 may execute the software. Memory 1103 may read the software from one or more other computer-readable media (such as mass storage device(s) 1135, 1136) or from one or more other sources through a suitable interface, such as network interface 1120. The software may cause processor(s) 1101 to carry out one or more processes or one or more steps of one or more processes described or illustrated herein. Carrying out such processes or steps may include defining data structures stored in memory 1103 and modifying the data structures as directed by the software.

The memory 1103 may include various components (e.g., machine readable media) including, but not limited to, a random access memory component (e.g., RAM 1104) (e.g., static RAM (SRAM), dynamic RAM (DRAM), ferroelectric random access memory (FRAM), phase-change random access memory (PRAM), etc.), a read-only memory component (e.g., ROM 1105), and any combinations thereof. ROM 1105 may act to communicate data and instructions unidirectionally to processor(s) 1101, and RAM 1104 may act to communicate data and instructions bidirectionally with processor(s) 1101. ROM 1105 and RAM 1104 may include any suitable tangible computer-readable media described below. In one example, a basic input/output system 1106 (BIOS), including basic routines that help to transfer information between elements within computer system 1100, such as during start-up, may be stored in the memory 1103.

Fixed storage 1108 is connected bidirectionally to processor(s) 1101, optionally through storage control unit 1107. Fixed storage 1108 provides additional data storage capacity and may also include any suitable tangible computer-readable media described herein. Storage 1108 may be used to store operating system 1109, executable(s) 1110, data 1111, applications 1112 (application programs), and the like. Storage 1108 can also include an optical disk drive, a solid-state memory device (e.g., flash-based systems), or a combination of any of the above. Information in storage 1108 may, in appropriate cases, be incorporated as virtual memory in memory 1103.

In one example, storage device(s) 1135 may be removably interfaced with computer system 1100 (e.g., via an external port connector (not shown)) via a storage device interface 1125. Particularly, storage device(s) 1135 and an associated machine-readable medium may provide non-volatile and/or volatile storage of machine-readable instructions, data structures, program modules, and/or other data for the computer system 1100. In one example, software may reside, completely or partially, within a machine-readable medium on storage device(s) 1135. In another example, software may reside, completely or partially, within processor(s) 1101.

Bus 1140 connects a wide variety of subsystems. Herein, reference to a bus may encompass one or more digital signal lines serving a common function, where appropriate. Bus 1140 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 1100 may also include an input device 1133. In one example, a user of computer system 1100 may enter commands and/or other information into computer system 1100 via input device(s) 1133. Examples of an input device(s) 1133 include, but are not limited to, an alphanumeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 1133 may be interfaced to bus 1140 via any of a variety of input interfaces 1123 (e.g., input interface 1123) including, but not limited to, serial, parallel, game port, USB, FIREWIRE, THUNDERBOLT, or any combination of the above.

In particular embodiments, when computer system 1100 is connected to network 1130, computer system 1100 may communicate with other devices, specifically mobile devices and enterprise systems, distributed computing systems, cloud storage systems, cloud computing systems, and the like, connected to network 1130. Communications to and from computer system 1100 may be sent through network interface 1120. For example, network interface 1120 may receive incoming communications (such as requests or responses from other devices) in the form of one or more packets (such as Internet Protocol (IP) packets) from network 1130, and computer system 1100 may store the incoming communications in memory 1103 for processing. Computer system 1100 may similarly store outgoing communications (such as requests or responses to other devices) in the form of one or more packets in memory 1103 and communicated to network 1130 from network interface 1120. Processor(s) 1101 may access these communication packets stored in memory 1103 for processing.

Examples of the network interface 1120 include, but are not limited to, a network interface card, a modem, and any combination thereof. Examples of a network 1130 or network segment 1130 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 1130, may employ a wired and/or a wireless mode of communication. In general, any network topology may be used.

In addition to a display 1132, computer system 1100 may include one or more other peripheral output devices 1134 including, but not limited to, an audio speaker, a printer, a storage device, and any combinations thereof. Such peripheral output devices may be connected to the bus 1140 via an output interface 1124. Examples of an output interface 1124 include, but are not limited to, a serial port, a parallel connection, a USB port, a FIREWIRE port, a THUNDERBOLT port, and any combinations thereof.

In addition or as an alternative, computer system 1100 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof configured to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. A storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 12:
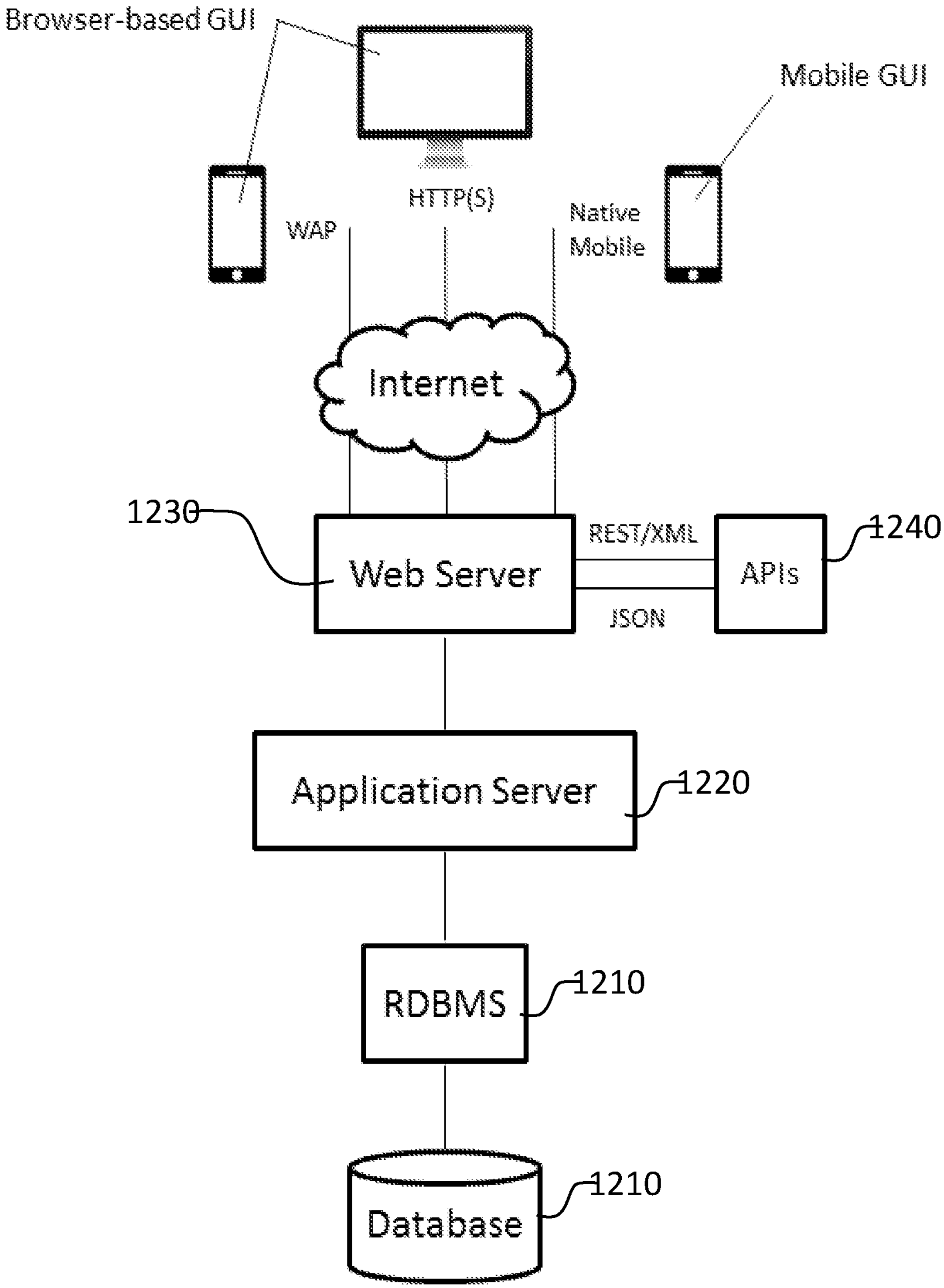
FIG. 12 shows a non-limiting example of a web/mobile application provision system; in this case, a system providing browser-based and/or native mobile user interfaces; per an embodiment herein.

Referring to FIG. 12, in a particular embodiment, an application provision system comprises one or more databases 1200 accessed by a relational database management system (RDBMS) 1110. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 1220 (such as Java servers, .NET servers, PHP servers, and the like) and one or more web servers 1230 (such as Apache, IIS, GWS and the like). The web server(s) optionally expose one or more web services via app application programming interfaces (APIs) 1240. Via a network, such as the Internet, the system provides browser-based and/or mobile native user interfaces.

Figure 13:
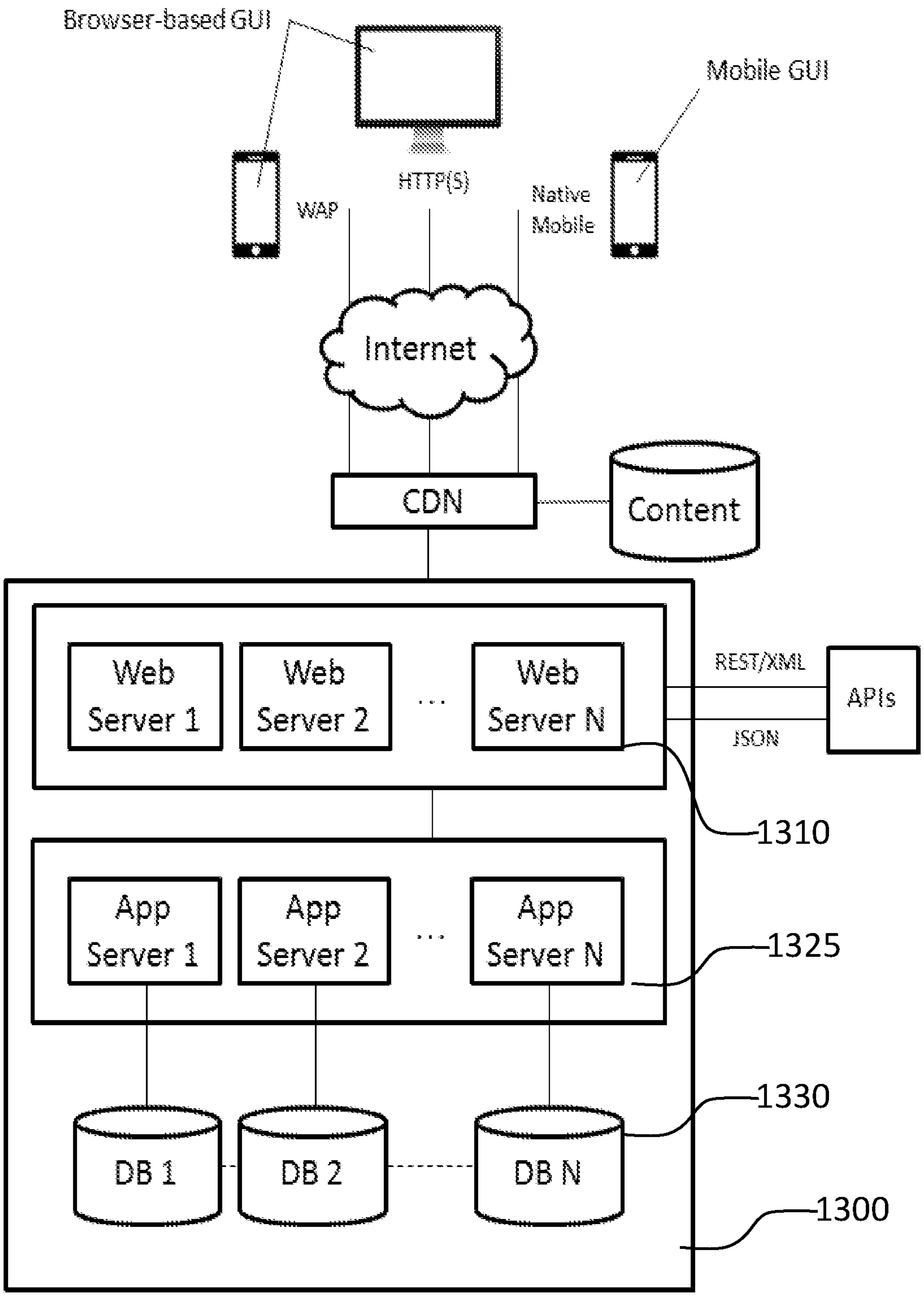
FIG. 13 shows a non-limiting example of a cloud-based web/mobile application provision system; in this case, a system comprising an elastically load balanced, auto-scaling web server and application server resources as well synchronously replicated databases; per an embodiment herein.

Referring to FIG. 13, in a particular embodiment, an application provision system alternatively has a distributed, cloud-based architecture 1300 and comprises elastically load balanced, auto-scaling web server resources 1310 and application server resources 1320 as well synchronously replicated databases 1330.

Mobile Application

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the methods, devices, systems, and platforms disclosed herein include one or more databases, or use of the same. In view of the disclosure provided herein, those of skill in the art will recognize that many databases are suitable for storage and retrieval of medical information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In a particular embodiment, a database is a distributed database. In other embodiments, a database is based on one or more local computer storage devices.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "in-ear" in some cases refers to being on or attached to the ear of a subject. As used herein, the term "in-ear" in some cases refers to being inside the concha of the ear of a subject. As used herein, the term "in-ear" in some cases refers to being inside an ear canal of the subject.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

EXAMPLES

The following illustrative examples are representative of embodiments of the software applications, systems, and methods described herein and are not meant to be limiting in any way.

Example 1

Judy is 88 years old, lives by herself, and is, for the most part, independent. However, she has started to fall regularly in recent months, sometimes from dizziness and sometimes from passing out after standing up. Judy is worried that she might eventually break her hip on one of these falls, and she's seen enough of her friends break their hips from falling to know where that leads. Not wanting to risk her ability to live independently, Judy puts the wearable device in her ear lobe and is surprised by its comfort and ease of use. She practically forgets that it is on most days. One night, Judy awakens with a need to go to the bathroom. As she sits up in her bed, the wearable device detects her movement and confirms that her body position has changed to sitting up and that she's intending to stand up. Because the device was measuring her blood pressure synchronously before she woke up, it already knew her blood pressure and blood volume were very low at that time of the night. Sensing that Judy's body is still waking up, the device determines she will have a significant CBF drop when she stands and that she's at high risk of a syncope event, and delivers an audible message recommending that Judy stay seated at her bedside for at least 30 more seconds before rising to her feet. This audible message is delivered within a second of the device detecting that Judy has begun the process of standing up. The responsiveness of the real-time message was possible in part because of the machine learning algorithm on the edge that was taking place at the device level.

Example 2

Sarah is 34 and recently gave birth to a baby boy. However, after the pregnancy, Sarah has often felt extremely lightheaded and her heart rate spikes by 50 beats per minute when she stands up, indicative of Postural Orthostatic Tachycardia Syndrome (POTS). She tries to increase her salt and water intake at her doctor's recommendation, but her body has trouble keeping the water in such that she's chronically dehydrated. The dehydration (or low blood volume) cause her CBF and HR to be unstable. Sarah discovers an in-ear wearable online that tells her how much her CBF drops and how much her HR spikes each time she stands. After buying the device, she finds the objective metrics useful to know when she really needs to stop what she's doing to take action to hydrate. For example, she generally will keep going about her day if her CBF only drops by 10% after she stands, but she knows she definitely shouldn't push it if she hears her CBF has dropped by 20%. One day, she hears her CBF has dropped by 25% so she immediately sits down, checks her device's app, and finds that her blood volume is very low. Sarah then drinks a liter of Gatorade to rehydrate and relaxes for 30 minutes before going about her day again. She explains to her friends who experience similar orthostatic symptoms that the device is exactly like how diabetics use Continuous Glucose Monitors (CGM) to manage their blood sugar to reduce hypoglycemic symptoms, except it helps her manage blood volume so that she can better manage her POTS symptoms.

Example 3

Grandpa Sam is 76 years old and enjoys meeting his friends each Wednesday at the deli, where they sit and talk for hours. Despite his doctor's recommendation, Sam is too proud to use a cane, but agrees to install an inconspicuous wearable device given his generally low blood pressure. As Sam is about to leave the table the next Wednesday, he hears a subtle alert to stand slowly, but finds that none of his friends have noticed. Upon complying, Sam notices that his usual dizziness after such periods of sitting have been greatly reduced.

Example 4

Exemplary audio messages are provided below:

"Your Blood Pressure is 94 over 62, which is a little low. Before you get out of bed, consider spending a minute sitting at your bedside with your legs off the bed, and stretching a bit. We should let your blood circulate before you get up! Have a good day!"

"I see you're getting up. Your blood pressure is low right now so you'll probably feel some dizziness. Please move slowly and be extra careful!"

Your Cerebral Blood Flow has dropped 10% . . . 15% . . . 20% . . . 25% . . . 35% . . . Please lower yourself immediately.

"Very little blood is getting to your head. You're at high risk of fainting and you're standing. Please slowly lower yourself immediately.

"I've noticed a trend that your blood pressure drops super low after lunch. This is beginning to happen right now. Drinking a tall glass of water will bring your blood pressure up quickly. Try drinking a glass, and I'll tell you how much it rises."

An exemplary text message to a loved one (or caretaker) is provided below:

"Just alerted your mom that she was at high risk of fainting. No worries, she sat down and didn't fall. She's given me permission to share her data with you. Her blood pressure has generally been stable as she's been getting a lot of steps in recently."

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A method of preventing presyncope, syncope and falls in a subject for execution by a wearable device that includes one or more processors, the method comprising:

generating, by one or more biometric sensors of the wearable device, biometric data regarding the subject, wherein the wearable device is configured to attach to an ear of the subject, wherein the wearable device is sized to fit entirely within the ear and is configured to be positioned entirely outside an ear canal of the ear such that the ear canal remains unobstructed during operation, and wherein the one or more biometric sensors are optical sensors configured to target at least one branch of a posterior auricular artery of the subject to monitor at least one biometric parameter of the subject;

aggregating and processing, by the one or more processors, the biometric data to produce processed data;

analyzing, by the one or more processors, the processed data to detect or predict an event relating to one or more of: poor cerebral blood flow, poor blood pressure, poor blood volume, poor blood oxygenation, presyncope, syncope, and a fall event; and delivering one or more real-time messages to the subject pertaining to the event.

2. The method of claim 1, wherein the biometric data comprises one or more measurements of: cerebral blood flow, blood pressure, blood volume, heart rate, heart rate variability, and blood oxygenation.

3. The method of claim 1, further comprising receiving activity data comprising one or more of: motion, body posture, change in body posture, activity level, and type of activity, and wherein the activity data is used to demarcate when a supine to standing transition has occurred in order to measure orthostatic changes in one or more of the biometric data and the processed data.

4. The method of claim 1, wherein analyzing the processed data comprises applying one or more artificial neural networks (ANNs).

5. The method of claim 1, wherein analyzing the processed data comprises one or more of:

identifying trends pertaining to the biometric data of the subject, identifying trends pertaining to the activity data of the subject, identifying trends pertaining to detected or predicted poor cerebral blood flow for the subject, identifying trends pertaining to detected or predicted presyncope events for the subject, identifying trends pertaining to detected or predicted syncope events for the subject, and identifying trends pertaining to detected or predicted fall events for the subject.

6. The method of claim 1, wherein the detecting or predicting of the event is based, at least in part, on one or more of: a user profile of the subject, the biometric data of the subject, activity data of the subject, one or more medical records of the subject, and a medical history of the subject.

7. The method of claim 1, wherein the one or more real-time messages comprise an audio message delivered utilizing an acoustic transducer of the wearable device configured to deliver real-time audio messages into the ear of the subject.

8. The method of claim 7, wherein the audio messages are delivered to the subject with low sound leakage perceived by others near the subject.

9. The method of claim 1, further comprising providing biometric feedback to the subject by delivering an audio message to the subject, wherein the audio message provides readings of biometric data at that moment.

10. The method of claim 1, wherein the one or more real-time messages comprise a measurement of one or more of: cerebral blood flow, blood pressure, blood volume, heart rate, heart rate variability, and blood oxygenation, and wherein the one or more real-time messages are read to the subject in real-time so the subject can determine if/when they should take action to avoid fainting.

11. The method of claim 1, wherein the one or more real-time messages comprise a measurement of one or more of: cerebral blood flow, blood pressure, blood volume, heart rate, heart rate variability, and blood oxygenation, and wherein the one or more real-time messages are read to the subject so the subject can determine whether the subject should increase hydration and/or salt intake in order to reduce symptoms.

12. The method of claim 1, wherein the one or more real-time messages comprise a visual message delivered utilizing a display of a device of the subject or a caretaker of the subject.

13. The method of claim 1, further comprising determining one or more visual messages for the subject.

14. The method of claim 13, wherein the one or more visual messages for the subject comprise biometric feedback, a behavioral coaching recommendation, an alert, or a warning.

15. The method of claim 1, further comprising providing a subject health portal application allowing access to real-time and historical biometric data and activity data and trends for the subject.

16. The method of claim 1, further comprising providing a healthcare provider portal application allowing access to real-time and historical biometric data and activity data and trends for one or more subjects.

17. A system for preventing presyncope, syncope and falls in a subject, the system comprising:

a wearable device configured to attach to an ear of the subject, wherein the wearable device is sized to fit entirely within the ear and is configured to be positioned entirely outside an ear canal of the ear such that the ear canal remains unobstructed during operation;

one or more biometric sensors of the wearable device, wherein the one or more biometric sensors are optical sensors configured to target at least one branch of a posterior auricular artery of the subject to monitor at least one biometric parameter of the subject and generate biometric data regarding the subject; and one or more processors of the wearable device configured to:

aggregate and process the biometric data to produce processed data;

analyze the processed data to detect or predict an event relating to one or more of: poor cerebral blood flow, poor blood pressure, poor blood volume, poor blood oxygenation, presyncope, syncope, and a fall event; and deliver one or more real-time messages to the subject pertaining to the event.

18. The system of claim 17, wherein the biometric data comprises one or more measurements of: cerebral blood flow, blood pressure, blood volume, heart rate, heart rate variability, and blood oxygenation.

19. The system of claim 17, further comprising an acoustic transducer of the wearable device configured to deliver real-time audio messages into the ear of the subject, wherein the one or more real-time messages comprise an audio message delivered utilizing the acoustic transducer.

20. The system of claim 19, wherein the audio messages are delivered to the subject with low sound leakage perceived by others near the subject.

* * * * *